US012584874B2

(12) United States Patent
Osswald et al.

(10) Patent No.: US 12,584,874 B2
(45) Date of Patent: Mar. 24, 2026

(54) GAS MEASURING DEVICE AND GAS MEASURING PROCESS FOR A TARGET GAS WITH IMPROVED COMPENSATION OF AN AMBIENT CONDITION

(71) Applicant: Drager Safety AG & Co. KGaA, Lübeck (DE)

(72) Inventors: Jürgen Osswald, Lübeck (DE); Tom Pöthig, Lübeck (DE); Sandra Balhorn, Lübeck (DE)

(73) Assignee: DRÄGER SAFETY AG & CO. KGAA, Lübeck (DE)

( * ) Notice: Subject to any disclaimer, the term of this patent is extended or adjusted under 35 U.S.C. 154(b) by 0 days.

(21) Appl. No.: 18/953,386

(22) Filed: Nov. 20, 2024

(65) Prior Publication Data

US 2025/0164425 A1     May 22, 2025

(30) Foreign Application Priority Data

Nov. 21, 2023   (DE) ......................... 102023132371.7

(51) Int. Cl.
G01N 25/30 (2006.01)
G01N 33/00 (2006.01)

(52) U.S. Cl.
CPC ......... G01N 25/30 (2013.01); G01N 33/0027 (2013.01)

(58) Field of Classification Search
CPC .............. G01N 25/30; G01N 33/0027; G01N 33/0006; G01N 27/16
See application file for complete search history.

(56) References Cited

U.S. PATENT DOCUMENTS

2009/0188297 A1* 7/2009 Willett ................... G01N 27/16
                                                         73/23.31
2018/0052124 A1   2/2018 Rogers et al.
                  (Continued)

FOREIGN PATENT DOCUMENTS

DE          4130099 A1    3/1993
DE     102006059566 A1    6/2008
              (Continued)

OTHER PUBLICATIONS

KR-20230084921-A (Year: 2023).*
JP-2017142274-A (Year: 2017).*

*Primary Examiner* — Kristina M Deherrera
*Assistant Examiner* — Fatemeh Esfandiari Nia
(74) *Attorney, Agent, or Firm* — McGlew and Tuttle, P.C.

(57) ABSTRACT

A gas measuring device (100) and a gas measuring process measure a concentration of a target gas. A detector detection variable sensor (12.1) measures a detection variable (U10) of a detector, which detector detection variable correlates with the concentration of the target gas in a gas sample (Gp). A compensator detection variable sensor (12.2) measures a detection variable (U11) of a compensator, wherein this compensator detection variable correlates less with the target gas concentration. The gas measuring device can be operated in a pressure-compensating mode and/or in a humidity-compensating mode. In pressure-compensating mode, the influence of the ambient pressure on a measurement result is compensated as best as possible under the boundary condition that the influence of the ambient humidity remains sufficiently small. In humidity-compensating mode, the influence of the ambient humidity on a measurement result is compensated as best as possible under a corresponding boundary condition.

19 Claims, 9 Drawing Sheets

(56)        References Cited

U.S. PATENT DOCUMENTS

| 2018/0335412 | A1 |    | 11/2018 | Zanella, Sr. et al. |
| 2020/0319155 | A1 | * | 10/2020 | Pratt ................. G01N 33/0031 |
| 2022/0381731 | A1 | * | 12/2022 | Rogers ................ G01N 27/121 |
| 2023/0349853 | A1 | * | 11/2023 | Santoro, Jr. ............ G01N 27/18 |

FOREIGN PATENT DOCUMENTS

| DE | 102017005713 | A1 |   | 12/2018 |  |
| DE | 102022102969 | A1 |   | 8/2022 |  |
| DE | 102022106689 | A1 |   | 10/2022 |  |
| JP | 2017142274 | A | * | 8/2017 |  |
| KR | 20230084921 | A | * | 6/2023 | ............ G01N 27/18 |

* cited by examiner

GAS MEASURING DEVICE AND GAS MEASURING PROCESS FOR A TARGET GAS WITH IMPROVED COMPENSATION OF AN AMBIENT CONDITION

CROSS REFERENCE TO RELATED APPLICATIONS

This application claims the benefit of priority under 35 U.S.C. § 119 of German Application 10 2023 132 371.7, filed Nov. 21, 2023, the entire contents of which are incorporated herein by reference.

TECHNICAL FIELD AND BACKGROUND

The invention relates to a gas measuring device and a gas measuring process which are configured to measure the concentration of a target gas and can be operated in different modes, wherein in each mode the influence of a non-directly measured ambient condition (environmental condition) on a detection variable is well compensated and wherein it depends on the mode which ambient condition is compensated.

In a preferred embodiment, the invention uses a principle known from the prior art, which has also become known as a "heat tone sensor". In this embodiment, the target gas is combustible, i.e. it can be oxidized. A detector is heated and heats a gas sample in a measuring chamber, the heating of the gas sample leads to oxidation of the combustible target gas in the gas sample, the oxidation releases thermal energy, the released thermal energy further heats the detector, and a detector detection variable, which correlates with the temperature of the detector, is measured. The further heating and thus the detector detection variable correlate with the sought concentration of combustible target gas.

The further heating of the detector depends not only on the target gas concentration, but also on ambient conditions. It is also known from the prior art to use a compensator that oxidizes less or no target gas, but ideally reacts to ambient conditions in the same way as the detector. A detection variable of the compensator is measured and used to compensate for the influence of ambient conditions on the detector detection variable.

The invention can also be applied to a gas measuring device that uses a different principle to measure the concentration of a target gas, in particular an optical measuring process with a radiation source and a photodetector (absorption spectroscopy) or an acoustic measuring process with a radiation source or sound source and an acoustic sensor or an electrochemical measuring process.

SUMMARY

It is an object of the invention to provide a gas measuring device and a gas measuring process which are configured to measure the concentration of a target gas and are able to compensate for the influence of an ambient condition on the measurement results better than known gas measuring devices and gas measuring processes, without necessarily requiring a sensor for these ambient conditions.

The problem is solved by a gas measuring device with features according to the invention and by a gas measuring process with features according to the invention. Advantageous embodiments of the gas measuring device according to the invention are, where appropriate, also advantageous embodiments of the gas measuring process according to the invention and vice versa.

The gas measuring device according to the invention is configured to measure the concentration of at least one target gas in a spatial area. In one application, the target gas is a combustible target gas, in another application it is another target gas that is harmful to human beings. The target gas can also be a gas that is vital for humans, such as oxygen, or can be carbon dioxide or an anesthetic. As a rule, the gas measuring device only provides at least one estimated value (approximate value) for the actual target gas concentration which may differ from the actual value. The gas measuring process according to the invention is carried out automatically and using a gas measuring device according to the invention.

A gas sample flows from the area to be monitored into the interior of the gas measuring device, where it reaches both a detector and a compensator of the gas measuring device. In one embodiment, a fluid conveying unit of the gas measuring device draws in (sucks) the gas sample; in another embodiment, the gas sample diffuses into the interior.

The detector has a measurable detector detection variable, e.g. electrical voltage or current. This detector detection variable correlates with the concentration of the target gas in a gas sample. A detector detection variable sensor of the gas measuring device is configured to measure the detector detection variable.

The compensator has a measurable compensator detection variable. The compensator detection variable correlates less than the detector detection variable or even not at all with the target gas concentration being sought. A compensator detection variable sensor of the gas measuring device is configured to measure the compensator detection variable. It is possible that a detection variable sensor is configured to measure a total detection variable that depends on both the detector detection variable and the compensator detection variable.

Note: The phrase that a sensor measures a physical quantity means the following: The sensor directly measures the physical quantity or another physical quantity that correlates with the quantity to be measured and is therefore an indicator of the quantity to be measured. In the present case, a detection variable is, for example, the temperature of a current-conducting component, and the sensor measures the electrical voltage and/or the electrical current.

The gas sample comes from a spatial area to be monitored. Ambient conditions, in particular the ambient temperature, in this spatial area have an influence on the gas sample. As a rule, the detector detection variable is therefore inevitably influenced by at least one ambient condition, in particular the ambient temperature. The compensator detection variable is also influenced by this ambient condition. However, the compensator detection variable correlates less than the detector detection variable with the target gas concentration and, in one embodiment, does not depend significantly on the target gas concentration. Ideally, both detection variables—optionally after a correction by one zero value each—depend in the same way on all ambient conditions. In practice, this ideal situation usually cannot be achieved.

A signal-processing evaluation unit is configured to automatically determine the concentration of the target gas in the gas sample. For this determination, the evaluation unit uses the measured detector detection variable, i.e. a signal from the detector detection variable sensor, and the measured compensator detection variable, i.e. a signal from the compensator detection variable sensor, and—if present—a signal from an optional sensor for an ambient condition. It is possible that the evaluation unit uses the respective signal from at least two ambient condition sensors. The step in which the evaluation unit determines the target gas concentration can also be described as a procedure in which the evaluation unit calculates an estimate for the actual target gas concentration. This step therefore at least approximately measures the actual target gas concentration.

The determined target gas concentration therefore depends on both the detector detection variable and the compensator detection variable. The compensator detection variable makes it possible to compensate to a certain extent for the influence of the ambient temperature and the influence of at least one other ambient condition on the detector detection variable.

In a preferred embodiment, a total detection variable is calculated by applying a functional relationship, which preferably comprises a weighted average of the measured detector detection variable and the measured compensator detection variable. The target gas concentration is determined as a function of the total detection variable.

As a rule, the gas measuring device according to the invention does not provide the actual target gas concentration as a measurement result, but an estimated value for the target gas concentration. In the following, the term "measurement result of the gas measuring device" or also the "determined target gas concentration" is used, whereby the determined target gas concentration generally deviates from the actual target gas concentration. The determined target gas concentration should deviate relatively slightly from the actual target gas concentration. How this goal is achieved according to the invention is described below.

The detector detection variable and thus the signal of the detector detection variable sensor depend on the one hand on the sought target gas concentration and on the other hand on three ambient conditions, namely the ambient temperature, the ambient humidity and the ambient pressure. The gas measuring device according to the invention can comprise a sensor for one ambient condition. As a rule, the compensator detection variable and thus the signal of the compensator detection variable sensor also depend on these three ambient conditions. The invention provides a way by which the respective influence of these three ambient conditions is taken into account without the gas measuring device necessarily having to have a sensor for each ambient condition.

The gas measuring device can be operated in at least one of at least two different modes. One of these modes is a pressure-compensating mode and one other of these modes is a humidity-compensating mode. During productive use, the gas measuring device is operated in at least one mode and at every time in exactly one mode. It is possible for it to be operated in two different modes during one productive use or during two consecutive uses.

In the pressure-compensating mode, the influence of the ambient pressure on a determination result of the evaluation unit is compensated as follows:

The boundary condition is met that the influence of the ambient humidity on the determination result remains below a specified upper humidity influence threshold. In other words, for each ambient humidity value that can occur when the gas measuring device is used, the determined concentration deviates from the actual target gas concentration by no more than the upper humidity influence threshold (limit). This upper threshold is specified, for example, in % LEL (lower explosive limit).

The influence of the ambient pressure on the determination result is compensated, with adherence to the boundary conditions just mentioned.

Accordingly, in the humidity-compensating mode, the influence of the ambient humidity on the determination result is compensated for as follows:

The boundary condition is met that the influence of the ambient pressure on the determination result remains below a specified upper pressure influence threshold.

The influence of the ambient humidity on the determination result is compensated for wherein this boundary condition is adhered to.

An ambient influence can in generally not be fully compensated, but an ambient influence can be compensated, that is compensated to an extent. The phrase "compensated" means: Prior to a productive use, the gas measuring device is calibrated by using a sample with several sample elements wherein every sample element comprises the target gas with a known target gas concentration. During the calibration the gas measuring device measures the respective target gas concentration of every sample element under known ambient conditions. During this calibration, the gas measuring device is calibrated such that the following effect is achieved: When the gas measuring device is applied to the sample, the influence of the ambient pressure (pressure-compensating mode) or of the ambient humidity (humidity-compensating mode) is compensated for as best as possible. With other words: The calibration process comprises an optimization procedure which is applied to the sample. During productive use, the gas measuring device does not necessarily achieve an optimal result under every possible combination of ambient conditions. The phrase that the "boundary condition is met" means that this boundary condition is met when the gas measuring device is applied to the sample. Preferably the gas measuring device is calibrated as follows: The influence of the ambient pressure (pressure-compensating mode) or of the ambient humidity (humidity-compensating mode) is compensated as best as possible wherein the boundary condition is met.

In the pressure-compensating mode, the determined target gas concentration depends in a first way on the detector detection variable and on the compensator detection variable, in the humidity-compensating mode in a second way. These two ways differ from each other. For example, the determined target gas concentration depends on a weighted average of the two detection variables, wherein at least one weighting factor is different for one mode than for the other mode.

Mention has already been made of an embodiment in which the evaluation unit determines the target gas concentration as a function of a total detection variable, wherein the total detection variable is calculated by applying a functional relationship to the two detection variables and wherein the functional relationship comprises a weighted average of the detector detection variable and the compensator detection variable. In the pressure-compensating mode, this functional relationship depends differently on the detector detection variable and/or on the compensator detection variable than in the humidity-compensating mode. For example, the weighting factor with which the detector detection variable is included in the functional relationship and/or the weighting factor of the compensator detection variable differ from mode to mode.

According to the invention, the gas measuring device can be operated in at least one of at least two different modes. In one embodiment, it can be operated in at least one of four different modes, namely additionally in a pressure-optimized mode and/or in a humidity-optimized mode. In the pressure-optimized mode, the influence of the ambient pressure on the determination result of the evaluation unit is compensated without complying with a boundary condition relating to another ambient condition. Similarly, in the humidity-optimized mode, the influence of the ambient humidity on the determination result is compensated without complying with a boundary condition relating to another ambient condition.

The at least two different modes make it possible to adapt the gas measuring device to a specific operating condition and to specific requirements for the accuracy of the detection result. For example, the ambient pressure is expected to fluctuate or oscillate greatly during use, while the ambient humidity remains approximately the same. This operating condition occurs, for example, when the target gas concentration is measured in a pipe with a gas mixture flowing through the pipe. The pressure of the gas mixture in the pipe can fluctuate greatly. For this reason, the gas measuring device is preferably operated in pressure-compensating mode or even in the optional pressure-optimized mode in this application.

If, on the other hand, the ambient humidity is expected to fluctuate or oscillate greatly while the ambient pressure remains approximately the same, the gas measuring device is preferably operated in the humidity-compensating mode or even in the optional humidity-optimized mode. This operating condition occurs, for example, when the target gas concentration is measured in a completely or at least largely enclosed space, for example in a measuring chamber or container.

In many cases, the invention avoids the need to make a compromise so that the gas measuring device can be used unamended and non-adapted for every possible operating condition. Such a compromise may have the effect that the gas measuring device does not provide a sufficiently good measurement result for some operating conditions.

The invention can be used in combination with at least one sensor for an ambient condition. However, the invention avoids the need for the gas measuring device to comprise a sufficiently reliable sensor for each ambient condition that has or could have an influence on the determination result, i.e. a temperature sensor, a humidity sensor, and a pressure sensor. The invention also eliminates the need to receive and process a signal with information about an ambient condition from a spatially distant sensor. The ambient conditions at the measuring position of this spatially remote sensor can differ significantly from the ambient conditions at the measuring position of the gas measuring device according to the invention.

In one embodiment, the gas measuring device can be optionally operated in any of the at least two, optionally four, different modes. Preferably, the setting in which mode the gas measuring device is operated is made exclusively by adapting the evaluation unit, i.e. generally by adapting the software. For example, at least one calculation rule that the evaluation unit uses to determine the estimated target gas concentrations by evaluating signals is accordingly adapted to the respective mode. The hardware, on the other hand, can in many cases remain the same for each possible mode in which the gas measuring device is or can be used. On the one hand, this feature makes it easier to implement the invention on an existing gas measuring device. On the other hand, this feature makes it possible to manufacture several gas measuring devices being identical in construction and then to set each of these identical devices for the respective mode. This procedure is in many cases more reliable, in particular due to possible series production, than the use of gas measuring devices with different hardware components for the different modes.

It is possible that a gas measuring device according to the invention is adapted to a mode in advance, i.e. during calibration and/or adjustment of the gas measuring device. It is possible that the gas measuring device can then only be used in this mode. In an alternative embodiment, however, the gas measuring device additionally comprises a selection unit. A user or a high-level control uses this selection unit to select one of at least two different possible modes. The gas measuring device is then operated in this mode. The user or control can later select a different mode using the selection unit. This embodiment makes it possible to use the same gas measuring device successively for different operating conditions without having to replace a component of the gas measuring device.

It is also possible that the gas measuring device automatically switches from one mode to another mode and measures an estimated value for the target gas concentration in at least two different modes, preferably each possible mode, one after the other.

As already mentioned, the detector detection variable and the compensator detection variable depend not only on the target gas concentration, but also on ambient conditions, in particular on the ambient temperature, the ambient humidity, and the ambient pressure. In one embodiment, the gas measuring device additionally comprises at least one sensor for an ambient condition, in particular a temperature sensor. The temperature sensor of the gas measuring device is configured to measure a temperature in the environment of the gas measuring device. The evaluation unit of the gas measuring device additionally uses a signal from the or each sensor for an ambient condition, for example a signal that includes information about the measured ambient temperature. It is possible that the gas measuring device comprises one sensor for each of at least two ambient conditions and that the evaluation unit uses two signals from these two sensors to determine the target gas concentration. Thanks to the invention, however, it is not necessary for the gas measuring device to comprise one sensor for each relevant ambient condition In a preferred embodiment, the gas measuring device comprises a temperature sensor, but neither a sensor for the ambient humidity nor a sensor for the ambient pressure. This configuration is advantageous in many applications, particularly for the following reason: As a rule, both a sensor for the ambient humidity and a sensor for the ambient pressure come into chemical and mechanical contact with the environment and therefore age relatively quickly, at least if no suitable and often relatively expensive countermeasures are taken. A temperature sensor, on the other hand, can be chemically and mechanically separated from the environment. As a rule, a thermal contact is sufficient.

In one embodiment, a sensor for an ambient condition can be optionally activated or deactivated, for example manually by a user or automatically by a control unit of the gas measuring device, whereby this sensor belongs to the gas measuring device. For example, the control unit or a user can deactivate a sensor for an ambient condition if it has been determined or detected that this sensor is defective. The fact that a sensor for an ambient condition is defective can be recognized in particular by a measured value of the sensor that lies outside a value range for the ambient condition that occurs in practice.

Or a user or the control unit deactivates a sensor for an ambient condition if the gas measuring device is to be used in an environment that is harmful or may be harmful to this sensor or if this sensor consumes a lot of electrical energy or is unable to provide a reliable measured value for the ambient condition in this environment. For example, the gas measuring device may comprise a temperature sensor, which is permanently active, as well as a pressure sensor and/or a humidity sensor, which is optionally activated or deactivated.

In a further variation of this embodiment, the gas measuring device comprises one sensor for each relevant ambient condition, i.e. in particular one sensor each for the ambient temperature, for the ambient humidity, and for the ambient pressure. Each of these sensors can be activated and deactivated, preferably independently of any other sensor. Preferably, a user can selectively activate or deactivate each sensor for an ambient condition. The embodiment in which the gas measuring device comprises a respective sensor for each relevant ambient condition facilitates the manufacture of several gas measuring devices according to the invention. These gas measuring devices all have the same hardware and in particular comprise the same sensors for the ambient conditions. To customize a particular gas measuring device, it is sufficient to activate or deactivate individual sensors. It is not necessary to manufacture gas measuring devices with different hardware.

In one embodiment, the gas measuring device can optionally be operated in a mode selection state, in which at least one of the two to four modes according to the invention or optional modes can be selected and used, or in a standard state, in which the evaluation unit determines the target gas concentration independently of a mode or in a default mode, or in which the gas measuring device measures the target gas concentration in each mode in succession, i.e. switches over automatically from one mode to another mode.

The embodiment with these two states can be combined with the embodiment in which at least one sensor for an environment is optionally activated or deactivated. A possible application of this combination is as follows: The gas measuring device comprises a pressure sensor that is selectively activated or deactivated. When the pressure sensor is activated, the evaluation unit uses the signal from the pressure sensor to take into account the influence of the ambient pressure on the determination of the target gas concentration. When the pressure sensor is deactivated, the gas measuring device is operated at least temporarily in the pressure-compensating mode. The same applies to a humidity sensor and the humidity-compensating mode. In the standard state, for example, the gas measuring device is configured to measure any ambient condition which is relevant to the measurement result. The corresponding sensor is therefore implemented and activated.

In one embodiment, the gas measuring device is configured as a so-called heat tone sensor. The detector comprises a heatable detector segment, and the gas measuring device is configured to heat the detector segment. In particular, the gas measuring device is configured to apply an electrical voltage to the detector segment, and the resulting flowing current heats the detector segment. The heated detector segment oxidizes combustible target gas, which has reached the detector as part of the gas sample—of course only if this gas sample contains a sufficient amount of combustible target gas. The oxidation of the target gas releases heat energy, and the released heat energy increases the temperature of the detector segment. Therefore, the temperature of the detector segment correlates with the target gas concentration.

The compensator comprises a heatable compensator segment. The gas measuring device is configured to heat the compensator segment. In a first alternative, the heated compensator segment is configured to oxidize less combustible target gas per unit of time than the heated detector segment, ideally no combustible target gas at all. In another embodiment, the gas measuring device is configured as follows: A smaller amount per unit of time of the gas sample reaches the compensator than the detector. These two alternatives can be combined with each other.

According to the invention, the gas measuring device comprises a detector detection variable sensor and additionally a compensator detection variable sensor. If the invention is applied to a heat tone sensor, the gas measuring device is configured as follows: The detector detection variable sensor measures the temperature of the detector segment. The compensator detection variable sensor measures the temperature of the compensator segment. The evaluation unit determines the target gas concentration depending on a signal from the detector detection variable sensor,
a signal from the compensator detection variable sensor,
optionally a signal from a temperature sensor and
optionally a signal from a humidity sensor and/or a signal from a pressure sensor.

In one implementation, a so-called bridge voltage is measured, which depends both on the voltage applied to the detector and on the voltage applied to the compensator, in particular in a Wheatstone measuring bridge. The evaluation unit determines the target gas concentration depending on the bridge voltage and optionally on the signal from the temperature sensor.

Ideally, the compensator reacts to ambient conditions in the same way as the detector, but is influenced less or not at all by a combustible target gas. Usually this ideal situation cannot be achieved in practice.

The configuration as a heat tone sensor eliminates the need to specify which target gases can occur in the area to be monitored and should be detected. Rather, a heat tone sensor is generally configured to detect any combustible target gas, provided the target gas concentration is sufficiently high. As a rule, a heat tone sensor can at least approximately determine the summed concentrations of all combustible target gases.

The gas measuring device can also be configured differently than just described. For example, the gas measuring device comprises a radiation source or sound source that is configured to emit electromagnetic radiation or sound and, as a detector, a receiver that is configured to generate a signal depending on the intensity of the impinging (incident) electromagnetic radiation or sound. The emitted radiation or sound penetrates a measuring chamber containing a gas sample to be analyzed. A target gas to be detected absorbs part of the radiation or sound in a certain wavelength range and therefore reduces the intensity of the impinging radiation or influences the speed of the impinging sound. The measured intensity acts as the detector detection variable. The detector detection variable sensor measures the intensity of the impinging radiation or sound. A reference receiver, for example, acts as the compensator, and the intensity of the radiation impinging on the reference receiver acts as the compensator detection variable. For example, suitable wavelength filters or mirrors are used to ensure that a target gas to be detected reduces the intensity of the radiation that impinges on the detector, but not the intensity of the radiation that impinges on the compensator. Such a gas measuring device is often referred to as an infrared-optical (photoelectric) gas measuring device and in many cases consumes less electrical energy than a heat tone sensor.

The invention can also be used, for example, in combination with a photoacoustic (infrared-acoustic) or electrochemical sensor.

A preferred implementation of an infrared-optical gas measuring device is described below. The radiation source emits electromagnetic radiation. The detector is a photodetector that generates a signal depending on the intensity of the impinging electromagnetic radiation and is referred to below as the target gas photodetector. The signal of the target gas photodetector depends not only on the target gas concentration, but also on at least one ambient condition. For example, both the target gas and water droplets and/or particles in the environment and thus in the gas sample absorb electromagnetic radiation.

Typically, the target gas to be detected absorbs electromagnetic radiation in a specific wavelength range. A wavelength filter is therefore preferably arranged between the radiation source and the photodetector, which only or at least predominantly allows radiation to pass in the wavelength range in which the target gas attenuates the electromagnetic radiation.

However, the wavelength range of the target gas can overlap with a wavelength range in which water droplets and/or particles attenuate radiation. In addition, a signal from the target gas photodetector can also be influenced by the ambient humidity and/or the ambient pressure. In a preferred implementation, the gas measuring device therefore additionally comprises a reference photodetector, which acts as the compensator detection variable sensor. A further wavelength filter allows electromagnetic radiation to pass in the wavelength range in which water droplets and/or particles attenuate radiation. The evaluation unit determines the target gas concentration depending on a signal from the target gas photodetector and a signal from the reference photodetector. Instead of two wavelength filters, it is also possible to provide two different radiation sources that emit electromagnetic radiation in different wavelength ranges.

The preferred embodiment has already been described in which the gas measuring device can be adapted to the respective mode solely by adapting or changing the evaluation unit. In one embodiment, a software program is adapted which the evaluation unit uses to determine the target gas concentration.

In one embodiment, the evaluation unit has permanent or at least temporary read access to a model that can be analyzed by a computer. This model is stored, for example, in a data memory of the gas measuring device or is a component of a program which the evaluation unit executes. The model comprises a functional relationship for the mode or for each mode in which the gas measuring device can be operated. The functional relationship for a mode describes a relationship between the target gas concentration on the one hand and
each detection variable, i.e. the respective signal of each detection variable sensor,
preferably the ambient temperature, i.e. the signal from the temperature sensor, and
optionally the ambient humidity and/or the ambient pressure, i.e. the signal from the humidity sensor and/or the signal from the pressure sensor on the other hand.

For example, the signal of the detector detection variable sensor and the signal of the compensator detection variable sensor occur in the functional model, and preferably also the signal of the temperature sensor and optionally the signal of the humidity sensor and/or the signal of the pressure sensor.

At a point in time, the gas measuring device is operated in one mode. In order to determine the target gas concentration in this mode, the evaluation unit applies (executes) the functional relationship that is valid for this mode to the respective signal of each detection variable sensor and preferably the signal of the temperature sensor. As a result, the evaluation unit provides a determined target gas concentration as the measurement result.

The invention also relates to a calibration device and a calibration process by means of which a gas measuring device according to the embodiment just described, i.e. with the functional model, can be calibrated.

The calibration device is configured to capture (record/acquire/detect) a specification (input/setting), which preferably comes from a user. The captured specification specifies at least one mode in which the gas measuring device to be calibrated should operate. It is possible that the specification specifies at least two different modes.

The calibration device is configured to automatically generate a model that can be evaluated by a computer. The generated model can be used by the evaluation unit of the gas measuring device. For the or each mode specified in the captured specification, the generated model comprises a functional relationship. The functional relationship for a mode describes, in a form that can be evaluated by a computer, a relationship between the target gas concentration on the one hand and
the respective signal of each detection variable sensor and
preferably the signal of the temperature sensor and
optionally a signal of another sensor for an ambient condition on the other hand.

To generate the model, the calibration device uses a predetermined sample and applies a set of predetermined possible functional relationships. In one implementation, each predetermined possible functional relationship has at least one model parameter, and the calibration device determines a value for each model parameter. When the gas measuring device is used, a parameter value is inserted into each possible functional relationship for the or each parameter. This turns the possible functional relationship into an actually applied (used) functional relationship. It is also possible that another learning process is applied to the sample, for example, a neural network is trained.

The used sample is determined empirically in advance and comprises several sample elements. Each sample element comprises an identification of an ambient condition-target gas combination and a signal value combination. The ambient condition-target gas combination is a combination of an ambient temperature,
an ambient pressure,
an ambient humidity and
an actual target gas concentration.

These four variables influence the or each detection variable, usually independently of each other. The signal value combination contains a respective value for the signal of each detection variable sensor and optionally for the signal of the temperature sensor, which respective value is measured at the ambient condition-target gas combination of the sample element. The actual target gas concentration of the sample element is specified or measured with another device and leads to the signal values of the detection variable sensors.

The calibration device is configured to perform the following steps for each specified mode and for each sample element:

Each possible functional relationship is applied to the signal value combination of the sample element. This application yields a resulting value for the target gas concentration.

The calculated value for the target gas concentration is compared with the actual value of the target gas concentration in this sample element.

Furthermore, the calibration device is configured to perform the following steps for each specified mode:

One of the given possible functional relationships is selected as the functional relationship that is actually used for this mode. To select a possible functional relationship, the comparison results are used, i.e. the results of the comparison between the calculated and the actual target gas concentration in the sample elements. For example, the functional relationship is used for which the calculated values for the target gas concentration deviate the least from the corresponding actual value.

The effect is that the selected functional relationship is used by the evaluation unit as the functional relationship that is actually used in this mode.

This configuration makes it possible to carry out the calibration empirically. It is not necessary to specify a complete analytical model that is used by the evaluation unit.

A further development of the embodiment with the functional model relates to an arrangement or combination with a first and a second gas measuring device, both implemented according to the invention. The first gas measuring device can be operated in the pressure-compensating mode, the second gas measuring device in the humidity-compensating mode. The evaluation unit of the first gas measuring device has read access to a first computer-evaluable model, the evaluation unit of the second gas measuring device has read access to a second computer-evaluable model. The first computer-evaluable model describes a dependence of the target gas concentration on the or each detection variable and preferably on the ambient temperature, and the gas measuring device fulfills the requirements for an operation in the pressure-compensating mode when using the first model. The second computer-evaluable model also describes a dependence of the target gas concentration on the or each detection variable and preferably on the ambient temperature, and the second model fulfills the requirements for an operation in the humidity-compensating mode.

The or a gas measuring device according to the invention can be configured as a mobile device, wherein a user carries this device with him/her while the user is in a spatial area. The device informs the user of the concentration of at least one target gas in the spatial area. Preferably, the mobile device has its own power supply unit and its own output unit. The or a gas measuring device according to the invention can also be configured as a stationary device, which is installed at a specific location in the spatial area and preferably transmits messages with measured target gas concentrations to a spatially remote receiver. The remote receiver outputs messages in at least one form that can be perceived by a human.

The invention is described below by means of embodiment examples. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF PREFERRED EMBODIMENTS

Figure 1:
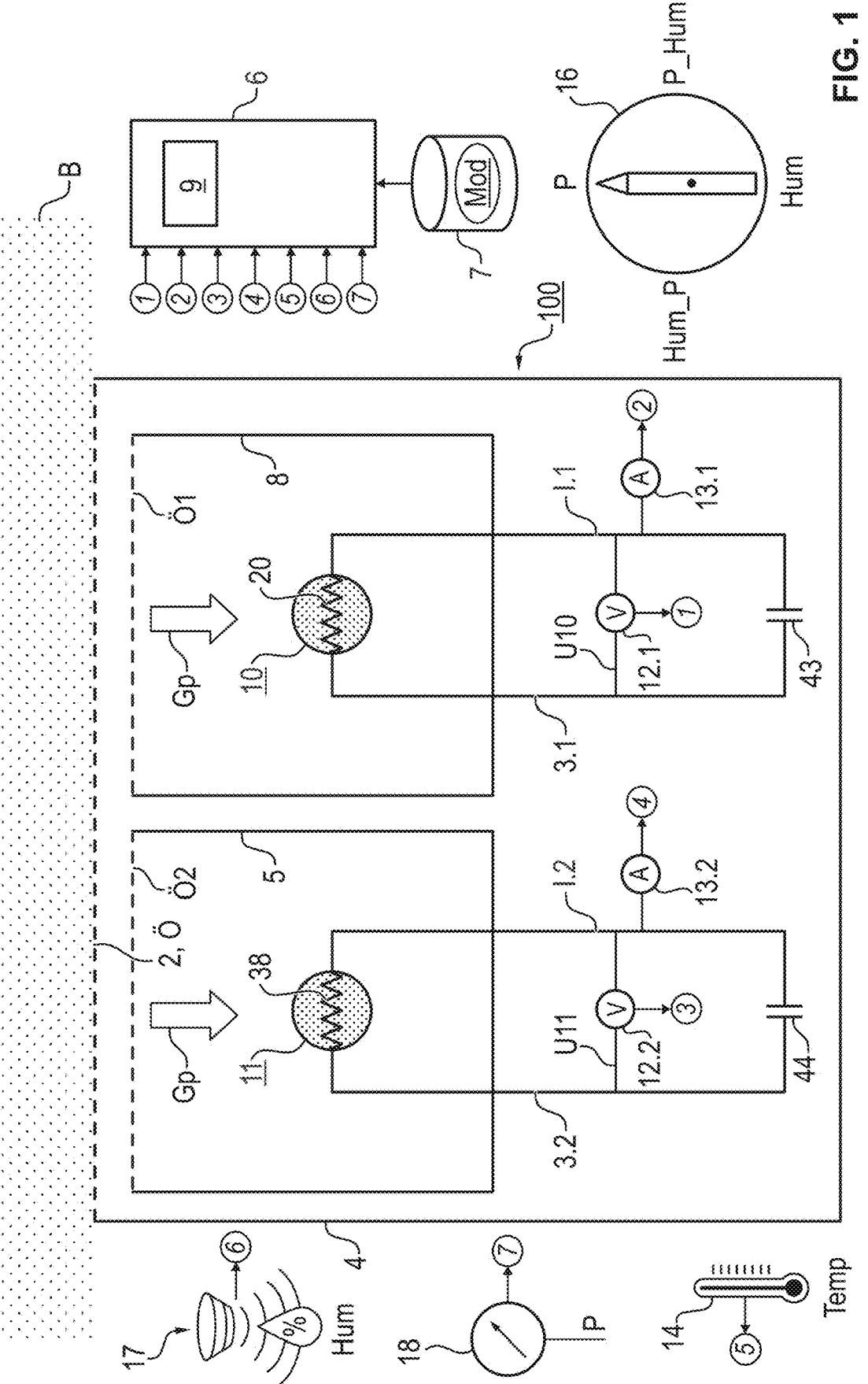
FIG. 1 is a schematic view of an exemplary configuration of the gas measuring device.

Referring to the drawings, in the embodiment examples, the gas measuring device according to the invention and the gas measuring process according to the invention are configured to monitor a spatial area for the presence of at least one combustible target gas and/or of at least approximately determining the concentration of a combustible target gas in this area. In one application, the gas measuring device is configured to measure a sum of the target gas concentrations in the presence of several combustible target gases. The gas measuring device uses a process known from the prior art to analyze a gas mixture in the spatial area.

In the embodiment example, the gas measuring device is configured as a stationary device that is positioned at a specific location in the area to be monitored during use. It is possible that several stationary gas measuring devices are arranged in this area. The or each gas measuring device is at least temporarily in a data connection with a remote receiver and transmits at least one signal to this receiver. The transferred signal comprises information about the measured target gas concentration. Preferably, the data connection is a wireless data connection, i.e. is implemented with radio waves. A wired data connection is also possible.

A detector is located inside a housing of the gas measuring device. Through an opening in the housing, a gas sample diffuses from the area to be monitored into the interior of the housing or is conveyed into the interior, e.g. sucked in by a pump or other fluid guidance unit.

In the embodiment example, the gas measuring device is configured as a heat tone sensor. Its principle was described at the beginning. The invention can also be applied to a gas measuring device comprising an infrared-optical or photoacoustic or electrochemical sensor.

The detector of the heat tone sensor comprises an electrically conductive wire with a heating segment. The heating detector segment is, for example, a coil that forms a segment of the wire. The electrically conductive material is, for example, platinum or rhodium or tungsten or an alloy using at least one of these metals. An electrical voltage U is applied to this wire so that an electric current flows through the wire. The flowing current heats the heating detector segment, and the heated heating detector segment emits thermal energy. The heat energy emitted causes at least one combustible target gas to be oxidized inside the housing—of course only if the spatial area and thus the gas sample inside contains a sufficient quantity of combustible target gas.

In one application, methane ($CH_4$) is a combustible target gas to be detected. When sufficient heat energy is added, methane reacts with oxygen to produce water and carbon dioxide. $CH_4$ and 2 $O_2$ thus become 2 $H_2O$ and $CO_2$.

During the oxidation of the target gas, thermal energy is released inside the housing. This thermal energy acts on the detector and increases the temperature of the heated wire through which the current flows. This temperature increase correlates with the released heat energy and thus with the concentration of the target gas inside the housing.

The change in temperature changes a measurable property of the detector that correlates with the detector temperature, for example the electrical resistance R of the detector wire through which the current flows. For many electrically conductive materials, it is known that the higher the temperature of the conductive material is, the higher is the electrical resistance. The gas measuring device measures at least one measurable variable which is influenced by the property and thus by the detector temperature and which is referred to below as the "detection variable". The detection variable is, for example, directly the temperature or a variable that correlates with the electrical resistance R of the wire, for example the electrical voltage U applied to the detector or the current I or the electrical power P absorbed by the detector wire. If a further measurable variable, which also depends on the electrical resistance R, is kept constant by a control system, the measured detection variable U or I or P correlates with the concentration of the target gas being sought. If, for example, the current I of the current flowing through the detector is kept constant, the electrical voltage U applied to the detector correlates with the electrical resistance R of the wire, the resistance R correlates with the temperature of the wire, the temperature of the wire correlates with the target gas concentration, and thus the measured electrical voltage U correlates with the target gas concentration sought—in the presence of several target gases with the combination (sum) of the target gas concentrations.

FIG. 1 shows an exemplary embodiment of a gas measuring device 100 according to the invention, which is able to monitor a spatial area B for the presence of at least one combustible target gas. In this embodiment, a detector 10 is arranged in a detector chamber 8. A compensator 11, described further below, is arranged in a compensator chamber 5. The two chambers 8, 5 are arranged in a housing 4. The detector chamber 8 and thus the detector 10 are in fluid communication with the area B to be monitored via an opening Ö1. The compensator chamber 5 and thus the compensator 11 are in a fluid connection with the area B via an opening Ö2. Thanks to the openings Ö1, Ö2, a gas sample Gp can pass from the area B into the interior of the housing 4 and there to the two chambers 8, 5.

An optional flame guard 2, for example a metallic grid, in front of the openings Ö1, Ö2 reduces the risk of flames from a chamber 8, 5 spreading outwards. Optionally, a thermal barrier (not shown) inside the gas measuring device 100 thermally separates the detector 10 from the compensator 11.

The electrical voltage U10 applied to the detector 10 causes an electrical current I to flow. The flowing current I heats the heating detector segment 20 to a working temperature, which is often between 400° C. and 500° C. However, this working temperature alone is usually not sufficient to oxidize a combustible target gas in the detector chamber 8. A higher working temperature is often undesirable because it could lead to uncontrolled burning or decomposition or even to an explosion of combustible target gas, which is often undesirable, and also consumes more electrical energy.

In order to be able to oxidize a combustible target gas despite a working temperature below 500° C., the detector 10 comprises a catalytic material which oxidizes the target gas in conjunction with the heated detector segment 20. A gas measuring device with such a detector 10 is therefore also referred to as a "catalytic sensor".

In a frequently used implementation, the heating detector segment 20 is surrounded by electrical insulation, for example by a ceramic coating. This electrical insulation electrically insulates the heating detector segment 20 and, in particular, prevents an undesired short circuit. The electrical insulation is thermally conductive so that the heating detector segment 20 can release thermal energy into the environment of the detector 10 and, conversely, thermal energy inside the detector chamber 8 can further heat up the heating detector segment 20. A coating of a catalytic material is applied to this electrical insulation. Or a catalytic material is embedded in the electrical insulation. This catalytic coating comes into contact with the gas mixture in the detector chamber 8 and thus also with a combustible target gas. A detector 10 constructed in this way is often referred to as a "pellistor".

Figure 2:
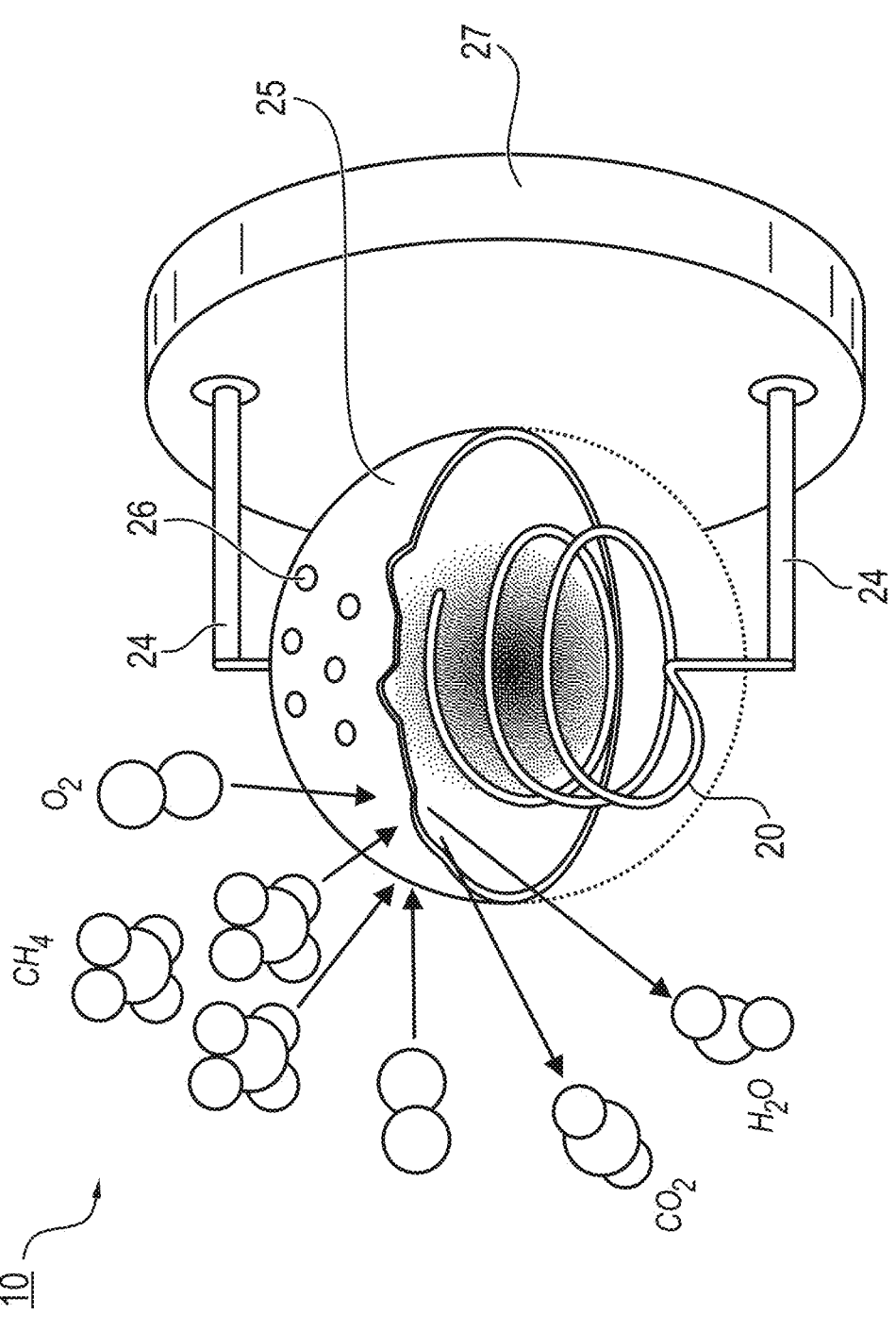
FIG. 2 is a perspective view of an exemplary configuration of the detector as a pellistor.

FIG. 2 shows an example of a detector 10 configured as a pellistor and a schematic diagram of the conversion of methane ($CH_4$) into $CO_2$ and $H_2O$. The detector 10 comprises a spirally wound and electrically conductive wire 20, which acts as a heating detector segment and is made of platinum, for example,
 a ceramic coating 25, which surrounds the heating detector segment 20 and has the shape of a full sphere in the example shown,
 a catalytic coating on the outer surface of the ceramic coating 25, which is indicated by circles 26 in FIG. 2,
 a mounting plate 27 and
 electrical contacts and mechanical holders 24 for the wire 20.

For example, platinum or palladium or rhodium or an alloy with at least one of these materials is used as the catalytic material. Alternatively or in addition to the catalytic coating, catalytic material 26 can also be embedded in the ceramic coating 25.

In a preferred embodiment, the full sphere of the detector 10 has a porous surface with a catalytic coating 26. In one embodiment, this porous surface is produced as follows: The detector 10 with the porous surface but without the catalytic coating is provided. The catalytic coating 26 is applied to the porous surface, and a portion of the catalytic material penetrates into the interior of the detector 10. Thanks to this porous surface, the detector 10 has a larger surface area compared to a smooth surface. Thanks to this larger surface area, the detector 10 is better able to oxidize combustible target gas, in particular because a larger amount of target gas comes into contact with the catalytic material. Thanks to the porous surface, a gas can reach deeper layers of the detector 10.

In one embodiment, the compensator 11 is constructed in the same way as the detector 10 and also comprises a heating segment, which is designated by the reference symbol 38. However, in one implementation, a smaller quantity per unit of time of gas can reach the compensator 11 than the detector 10. In another embodiment, the compensator 11 comprises no catalytic coating 26 or a catalytic coating 26 that is configured to oxidize less target gas per unit of time than the detector 10.

Figure 3:
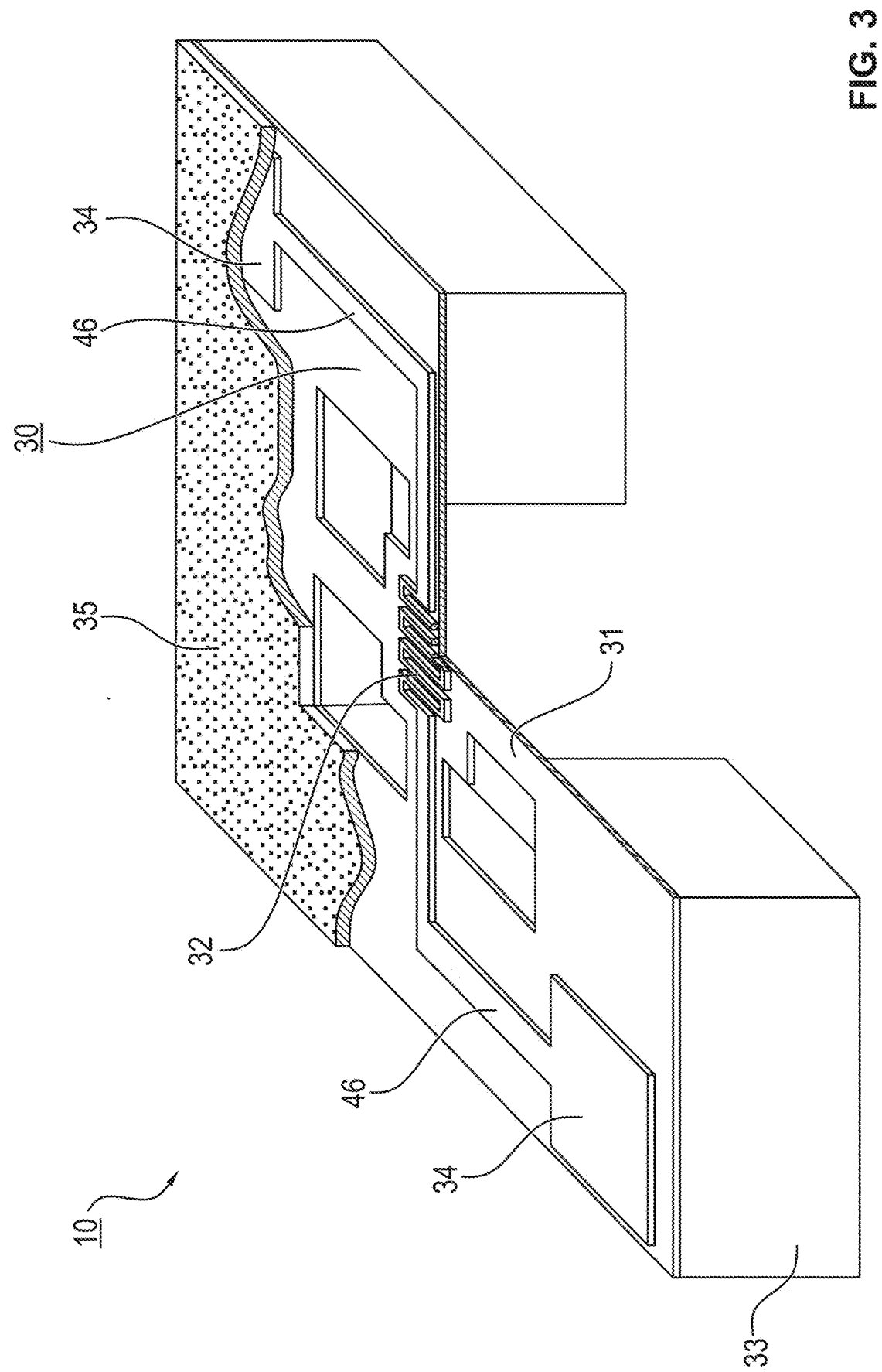
FIG. 3 is a perspective view of an exemplary alternative configuration of the detector as a flat component.
Figure 4:
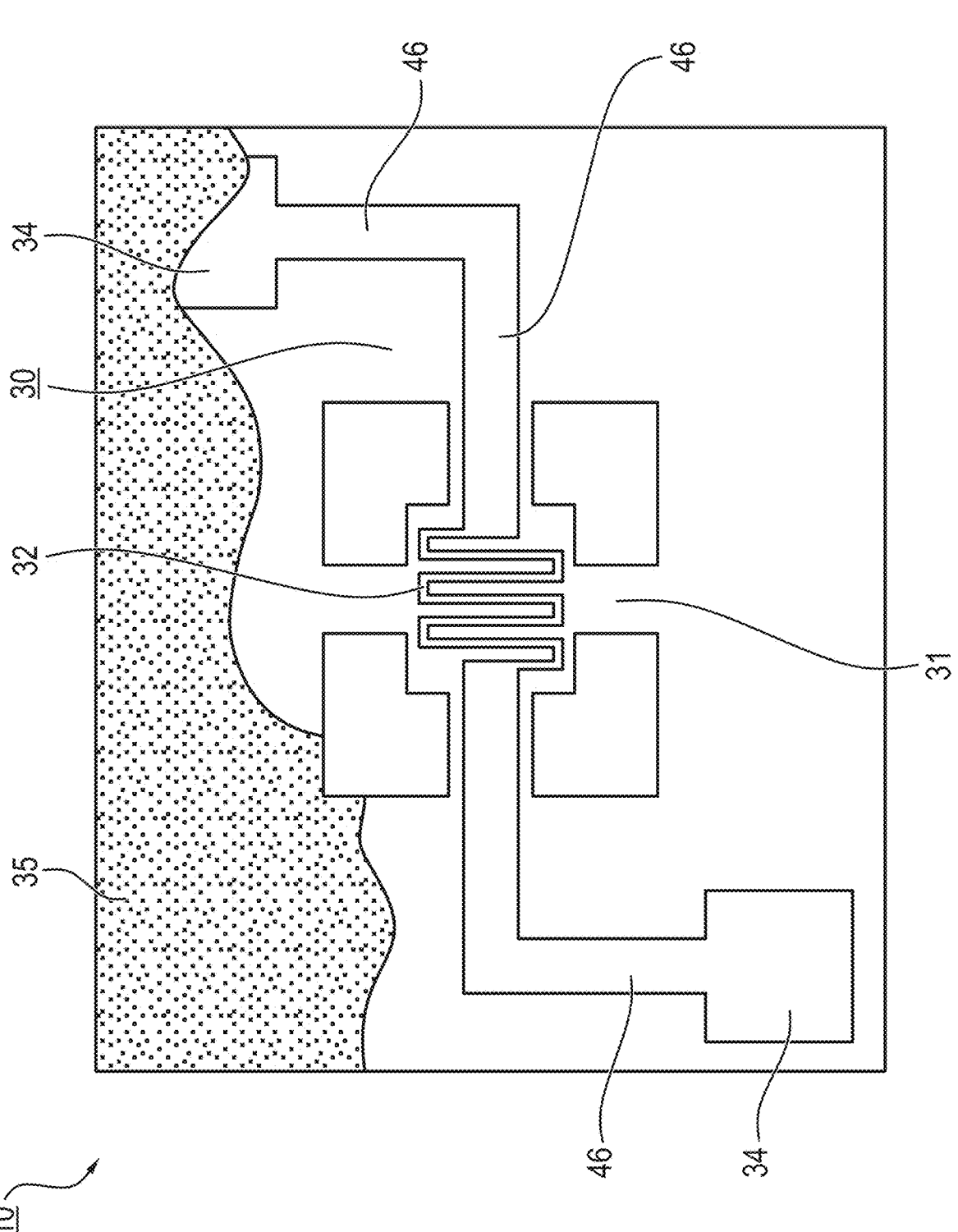
FIG. 4 is a top view of the detector in FIG. 3.

FIG. 3 and FIG. 4 show a different configuration of the detector 10 in a perspective view (FIG. 3) and in a top view (FIG. 4). The detector 10 comprises the following components:

an electrically conductive component 30 with a heating segment 32 and an electrical contact 46, wherein the component 30 has the form of a conductor line (path, track), a protective layer 35, a support plate 31 extending in a plane, this plane being oblique to the drawing plane of FIG. 3 and lying in the drawing plane of FIG. 4, a wafer substrate 33, which carries the carrier plate 31, and electrical contact points 34 for the electrically conductive component 30.

The protective layer 35 covers at least the conductor track (trace) 30, preferably the entire carrier plate 31, and prevents the conductor track 30 from coming into direct contact with a gas mixture. In one embodiment, the protective layer 35 is made of silicon nitride. A catalytically active material is applied to the protective layer 35, at least in an area above the heating segment 32.

The compensator 11 can again be constructed in the same way as the detector 10 of FIG. 3 or and FIG. 4 or have less or even no catalytically active material.

However, the temperature of the detector 10 and thus also the or each detection variable is not only influenced by the thermal energy released, but also by the ambient conditions in the area B to be monitored. The three main ambient conditions are the ambient temperature Temp, the ambient pressure P, and the ambient humidity Hum. In particular, both the zero point of the detector 10 and the increase in the detector temperature depend not only on the target gas concentration, but also on the ambient temperature Temp. The zero point is the value that the detector detection variable assumes when no target gas is present. These three ambient conditions Temp, P, Hum can also change the conditions inside the housing 4 and thus also in the detector chamber 8. These ambient conditions can also influence the detector temperature and thus a detection variable U10, for example because the thermal conductivity in the environment of the detector 10 is changed.

It is desirable that the gas measuring device 100 is able to reliably detect a combustible target gas despite of varying ambient conditions on the one hand and on the other hand generates only a few false alarms, i.e. only rarely determines that a target gas is present, although in reality no target gas has occurred above a detection threshold, which is an erroneous result.

Note: The three ambient conditions temperature, pressure, and humidity are designated as Temp, P, Hum. Values of these three ambient conditions are designated as temp, p, hum.

The gas measuring device 100 according to the invention is configured to compensate to a certain extent for the influence of the three ambient conditions Temp, P, Hum on the detection variable. In the following description, the current strength I.1 is kept constant by closed-loop control, and the electrical voltage U10 applied to the detector 10 serves as the detection variable. As already mentioned, this detection variable U10 depends on the temperature of the heating detector segment 20. This temperature in turn depends on the one hand on the target gas concentration and on the other hand on the three ambient conditions just mentioned.

In order to compensate for the influence of ambient conditions, the gas measuring device 100 comprises in addition to the detector 10 the aforementioned compensator 11 in the compensator chamber 5, see FIG. 1. The compensator 11 also comprises a wire with a heating compensator segment 38. An electrical voltage U11 is also applied to the compensator 11, so that electrical current 1.2 flows and the heating segment 38 of the compensator 11 is also heated. The compensator 11 is also exposed to the varying ambient conditions.

In one embodiment, the compensator 11 also comprises a spirally wound and electrically conductive wire, which acts as a heating compensator segment and is designated by the reference sign 38. The compensator 11 also comprises a ceramic sheath, a mounting plate, electrical connections, and mechanical brackets. In one embodiment, however, the ceramic coating of the compensator 11 is not provided with a catalytic coating, in contrast to the detector 10.

In another implementation, the compensator 11 is constructed in the same way as the detector 10, i.e. it also comprises a ceramic coating. This ceramic coating is also catalytically active in the other implementation. However, the gas measuring device 100 is configured in such a way that in a unit of time less gas can pass from the area B to be monitored to the compensator 11 than to the detector 10.

As an alternative, the heating segment 38 of the compensator 11 is heated to a lower temperature than the heating segment 20 of the detector 10.

FIG. 1 shows the compensator 11 in the compensator chamber 5. It can be seen that the detector 10 comprises the heating detector segment 20 and the compensator 11 comprises the heating compensator segment 38. In the example shown, the compensator 11 is also configured as a spherical pellistor, but unlike the detector 10, it does not have a catalytically active coating 26.

In the implementation shown in FIG. 1, the detector 10 is supplied with electrical energy from a voltage source 43, the compensator 11 from a voltage source 44. A detector circuit 3.1 comprises the detector 10 and the voltage source 43, a compensator circuit 3.2 comprises the compensator 11 and the voltage source 44. Because two independent circuits 3.1 and 3.2 are implemented, the electrical voltage U11 applied to the compensator 11 may differ from the electrical voltage U10 applied to the detector 10, and the strength of the current flowing in the compensator circuit 3.2 may differ from the strength of the current flowing in the detector circuit 3.1. The two voltage sources 43, 44 are preferably implemented with rechargeable batteries (accumulators). It is possible that the same power supply unit acts as both the first voltage source 43 and the second voltage source 44.

A voltage sensor 12.1 measures the electrical voltage U10 applied to the detector 10. An amperage sensor 13.1 measures the intensity I.1 of the electric current flowing through the circuit 3.1 for the detector 10. A voltage sensor 12.2 measures the electrical voltage U11 applied to the compensator 11. An amperage sensor 13.2 measures the intensity I.2 of the electric current flowing through the circuit 3.2 for the compensator 11.

Ideally, a combustible target gas acts only on the detector 10, while the ambient conditions act in the same way on the detector 10 and the compensator 11. If these ideal conditions are met, the difference between the detector detection variable U10 and the compensator detection variable U11— optionally corrected by a respective zero value—is a reliable indicator of the desired concentration of the target gas, for every possible combination of ambient conditions.

However, usually this ideal condition is not fulfilled in practice. One reason is that the detector 10 and the compensator 11 react differently to ambient conditions already due to design-related differences and/or unavoidable manufacturing tolerances. These differences are particularly relevant if the compensator 11 has less catalytically active material than the detector 10 or even no catalytically active material at all. Another reason is that the oxidation of target gases often leads more strongly to deposits on the surface of the detector 10 than on the surface of the compensator 11. In the following, an embodiment according to the invention is described as to how the gas measuring device 100 can reliably measure the target gas concentration in many cases despite these differently acting ambient conditions.

According to a preferred embodiment, the gas measuring device 100 measures the ambient temperature, preferably at a measuring position on an outer surface of the gas measuring device 100. The invention can also be implemented without the gas measuring device 100 comprising a temperature sensor.

In the embodiment example shown, a temperature sensor 14 of the gas measuring device 100 is configured to measure the ambient temperature Temp. In the embodiment example, the temperature sensor 14 provides the temperature difference $\Delta$Temp between the current ambient temperature and a specified reference ambient temperature of 20° C., for example. The temperature sensor 14 provides an analog or digital signal that includes information about the ambient temperature Temp—in the embodiment example with the temperature difference $\Delta$Temp. The influence of the ambient temperature Temp on the detection variable is computationally compensated to a certain extent with the aid of a signal from the temperature sensor 14.

In one embodiment, the gas measuring device 100 of FIG. 1 comprises a sensor 17 for the ambient pressure P and a sensor 18 for the ambient humidity Hum. In one application, the sensors 17, 18 can have a relatively simple structure, so that the ambient humidity Hum and/or the ambient pressure P are only measured with a relatively large measurement error. In another application, each sensor 17, 18 can be activated and deactivated. For example, a user deactivates a sensor 17 or 18 if the gas measuring device 100 is or will be used in an environment in which the activated sensor 17 or 18 can be damaged, for example due to a very high pressure or humidity or a certain gas in the environment. It is also possible that a sensor 17, 18 is defective and the gas measuring device 100 is still to be used.

How the influence of the ambient pressure P and the ambient humidity Hum can nevertheless be compensated for, at least to a certain extent, is described below.

Preferably, the gas measuring device 100 comprises a reliable sensor 14 for the ambient temperature Temp, but only a relatively simple and/or deactivatable or no sensor 18 for the ambient pressure P and a relatively simple and/or deactivatable or no sensor 17 for the ambient humidity Hum. In particular this preferred embodiment has the advantage described below: A temperature sensor 14 can be chemically insulated from the environment by insulating material with good thermal conductivity. The temperature sensor 14 is configured to measure the ambient temperature Temp relatively reliably, but is not directly exposed to the other ambient conditions. Both a pressure sensor and a humidity sensor, on the other hand, generally have to be in a fluid connection with the environment, i.e. with the spatial area B to be monitored, and can therefore be exposed to combustible target gases and other potentially harmful substances over a very long period of time. A sensor that is in a fluid connection with the environment and yet is sufficiently robust and reliable is often relatively expensive and/or heavy and/or requires a relatively large amount of electrical energy. A temperature sensor does not have this disadvantage, or at least only to a lesser extent.

A schematically shown signal-processing control unit 6 with an evaluation unit 9 receives signals from the sensors 12.1, 12.2, 13.1, 13.2, 14, 17, 18 and determines the current concentration of a combustible target gas in the monitored area B, i.e. derives an estimated value. This estimated value is usually variable over time. If several combustible target gases are present in the area B, in the embodiment example the estimated value describes the summed concentrations of these combustible target gases. The control unit 6 and thus the evaluation unit 9 have at least temporary read access to a data memory 7, in which an evaluation program and/or a computer-evaluable model Mod with several functional relationships are stored.

It would be ideal if the gas measuring device 100 could fully compensate for the influence of all three ambient conditions, i.e. both the influence of the ambient temperature Temp and the influence of the ambient pressure P as well as the influence of the ambient humidity Hum, using only the compensator 11 and the temperature sensor 14, for each possible value of these three ambient conditions during an application. In practice, however, this is generally not possible, at least not if the ambient pressure P and/or the ambient humidity Hum can vary considerably during use and neither a pressure sensor nor a humidity sensor are present and activated. A key reason for this is that in many cases the compensator 11 and the detector 10 react differently to at least one ambient condition, in particular due to design or construction-related differences or unavoidable manufacturing tolerances.

In the example embodiment, a value range is specified for each of the three ambient conditions temperature Temp, humidity Hum and pressure P. The value range for the temperature ranges from $Temp_{min}$ to $Temp_{max}$, the value range for the humidity ranges from $Hum_{min}$ to $Hum_{max}$ and the value range for the pressure ranges from $P_{min}$ to $P_{max}$. The gas measuring device 100 achieves the effect described below if each of these three ambient conditions lies within the specified value range.

The gas measuring device 100 of the embodiment example can optionally be operated in one of four possible different modes. In one embodiment, one of these four modes is selected during the configuration of the gas measuring device 100 and is implemented using appropriate software. The model Mod in the data memory 7 is then valid for this selected mode. The gas measuring device 100 cannot necessarily be switched from one mode to another during operation.

In another embodiment, however, the gas measuring device 100 comprises a switch 16, shown schematically, with which a user can select one of these four possible modes. The user operates the switch 16 to switch from one mode to another mode. This switch 16 can be implemented, for example, as a mechanical switch or with the aid of a touch-sensitive screen (touch screen) or with the aid of several buttons. For each mode a respective model is stored in the data memory 7.

In a further embodiment, the gas measuring device 100 switches automatically from one mode to the other during operation, so that it is operated in each of the possible modes during use. In each mode, the gas measuring device 100 determines an estimated value for the target gas concentration. As a rule, the estimated values differ from mode to mode. A preferred embodiment for deriving an estimated value and preferably displaying it to a user is as follows: As long as an estimated value that is determined in a mode is within a predetermined target concentration range, this estimated value is output. Or no message is issued at all or the message that there is no impermissible target gas concentration. If, on the other hand, at least one estimated value is outside the specified target concentration range, the estimated value that is furthest away from the specified target concentration range is output, i.e. the largest estimated value of a dangerous target gas or the smallest estimated value of a vital target gas, e.g. oxygen. With this configuration, you are "on the safe side".

The following four modes are distinguished in the example:

P The influence of the ambient pressure P is compensated for (pressure-optimized mode)—the ambient pressure P is compensated with the provided configuration (i.e., the ambient pressure P is compensated).

Hum The influence of the ambient humidity Hum is compensated for (humidity-optimized mode)—the ambient humidity Hum is compensated with the provided configuration (i.e., the ambient humidity Hum is compensated).

P_Hum The influence of the ambient pressure P is compensated for while maintaining a boundary condition relating to the ambient humidity Hum (pressure-compensating mode)—the ambient pressure P is compensated with the provided configuration to not surpass the boundary condition relating to the ambient humidity Hum (i.e., the ambient pressure P is compensated under the boundary condition).

Hum_P the influence of the ambient humidity is compensated for while maintaining a boundary condition relating to the ambient pressure P (humidity-compensating mode)—the ambient humidity Hum is compensated with the provided configuration to not surpass the boundary condition relating to the ambient pressure P (i.e., the ambient humidity Hum is compensated under the boundary condition).

The boundary condition relating to the ambient humidity Hum is predefined and specifies, for example, that the measured value con for the target gas concentration Con varies by a maximum of x % if the ambient humidity Hum remains within the predefined humidity range from $Hum_{min}$ to $Hum_{max}$ and if the actual target gas concentration remains constant. During use, the ambient humidity Hum is always within this humidity range. The corresponding effect applies to the boundary condition relating to the ambient pressure P, i.e. the ambient pressure is in the range from $P_{min}$ to $P_{max}$.

The gas measuring device 100 can therefore be operated in one of four possible modes. This allows the gas measuring device 100 to be adapted to different operating conditions.

One possible operating condition is as follows: The target gas concentration in a pipe is to be measured, with a gas mixture flowing through this pipe. In this operating condition, the ambient pressure P can fluctuate greatly, which is why the P mode or the P_Hum mode are useful.

Another possible operating condition is the following: The target gas concentration in an enclosed space is to be measured. This enclosed space is only in a fluid connection with the environment via a relatively small opening and is, for example, a container for fluids. Or the enclosed space is a test chamber or measuring chamber in which different ambient conditions and, in particular, different humidity levels are generated in order to test a component. In this other operating condition, the ambient humidity Hum can fluctuate greatly, which is why Hum mode or Hum_P mode are useful.

The invention makes it possible to manufacture a quantity of identical gas measuring devices and to adapt each gas measuring device 100 of this quantity to the respective operating conditions by selecting one of the four possible modes. The selection is made in advance or during operation. Operation in a specific mode requires the implementation or selection of software, while the hardware remains unchanged. In many cases, this embodiment increases reliability and reduces design, construction and manufacturing costs compared to an embodiment in which at least two sets of different gas measuring devices are manufactured, one set for each operating condition.

In the following illustration, the electrical detector voltage U10 applied to the detector 10 acts as the detection variable that correlates with the temperature of the heating segment 20 of the detector 10, see FIG. 1. The current I.1 is kept constant. Accordingly, the electrical compensator voltage U11 applied to the compensator 11 acts as the detection variable that correlates with the temperature of the heating segment 38 of the compensator 11. The current 1.2 is kept constant.

The three sensors 14, 17 and 18 also each provide an electrical signal—of course only if they are actually present, intact and activated. This signal is referred to as U($\Delta$Temp), U(Hum), and U($\Delta$P). In the embodiment example, the assumption is used that the three ambient conditions ambient temperature Temp, ambient humidity Hum and ambient pressure P each have a linear effect on the detection variables. Therefore, for each of these three ambient conditions a proportionality factor is determined in advance, preferably empirically, and used in the application.

Depending on the values for the five variables U10, U11, U($\Delta$Temp), U(Hum), U($\Delta$P), the evaluation unit 9 calculates a value for a total detection variable Det. In doing so, the evaluation unit 9 applies the calculation rule $$Det = F[U10, U11, U(\Delta Temp), U(Hum), U(\Delta P)]. \qquad (1)$$

In one embodiment, the function F depends on at least one respective parameter for U10 and U11, optionally on at least one further parameter. In a preferred implementation of this embodiment, the calculation rule (1) has the form $$Det = U10 - \alpha * U11 - \beta * U(\Delta Temp) - \gamma * U(Hum) - \xi * U(\Delta P) - x0. \qquad (2)$$

with a gain factor (amplification factor) $\alpha$ for the compensator voltage U11, a gain factor $\beta$ for the signal U($\Delta$Temp) of the temperature sensor 14, a gain factor $\gamma$ for the signal U(Hum) of the humidity sensor 17, a gain factor $\xi$ for the signal U($\Delta$P) of the pressure sensor 18 and a zero value x0. The gain factor $\alpha$ compensates to a certain extent for design-related differences between the detector 10 and the compensator 11 and is preferably greater than 1.1. The gain factor β compensates to a certain extent for the influence of the ambient temperature Temp on the total detection variable Det, which is assumed to be linear. Accordingly, the factors γ and ξ compensate for the influence of the ambient humidity Hum and the ambient pressure ΔP, resp., which influences are also assumed to be linear.

If neither a humidity sensor 17 nor a pressure sensor 18 is present or both sensors 17, 18 are deactivated or defective, the following calculation rule is applied:

$$Det = U10 - \alpha * U11 - \beta * U(\Delta Temp) - x0. \quad (3)$$

with a different factor x0 than in the calculation rule (2).

The parameters of the function F in the calculation rules (1) to (3) are calculated empirically using a random sample. It is also possible that the function F has the form of a neural network or is generated by another machine learning process.

The evaluation unit 9 calculates a value for the target gas concentration Con from the value for the total detection variable Det. For doing so, it applies the calculation rule $$Con_{meas} = F_{Con}(Det). \quad (4)$$

For example $$Con_{meas} = \gamma * Det_{Con} \quad (5)$$

with an empirically determined factor $\gamma_{con}$. Note: Con is the actual target gas concentration, $Con_{meas}$ is the measured value. Ideally, $Con_{meas}$=Con.

Preferably, the calculation rule (4) or (5) is defined such that a value of zero for the total detection variable Det leads to a value of zero for the target gas concentration Con.

Both the function F and the function $F_{Con}$ are stored in the data memory 7 in a suitable manner for computer evaluation and form part of the model Mod.

Depending on the used mode, the evaluation unit 9 uses a function $F_P$, $F_{P\_Hum}$, $F_{Hum}$ or $F_{Hum\_P}$ as the function F in the calculation rule (1). If the calculation rule (2) or (3) is used, a gain factor $\alpha_P$, $\alpha_{P\_Hum}$, $\alpha_{Hum}$ or $\alpha_{Hum\_P}$ is used as the gain factor α for the compensator voltage U11, depending on the mode. Accordingly, a gain factor $\beta_P$, $\beta_{P\_Hum}$, $\beta_{Hum}$ or $\beta_{Hum\_P}$ is used as the gain factor β for the signal U(ΔTemp) of the temperature sensor 14. In one embodiment, four different zero values are used accordingly; in another embodiment, the same zero value x0 is always used regardless of the mode.

Figure 5:
FIG. 5 is a graph showing a boundary condition for the dependence on the ambient temperature.
Figure 6:
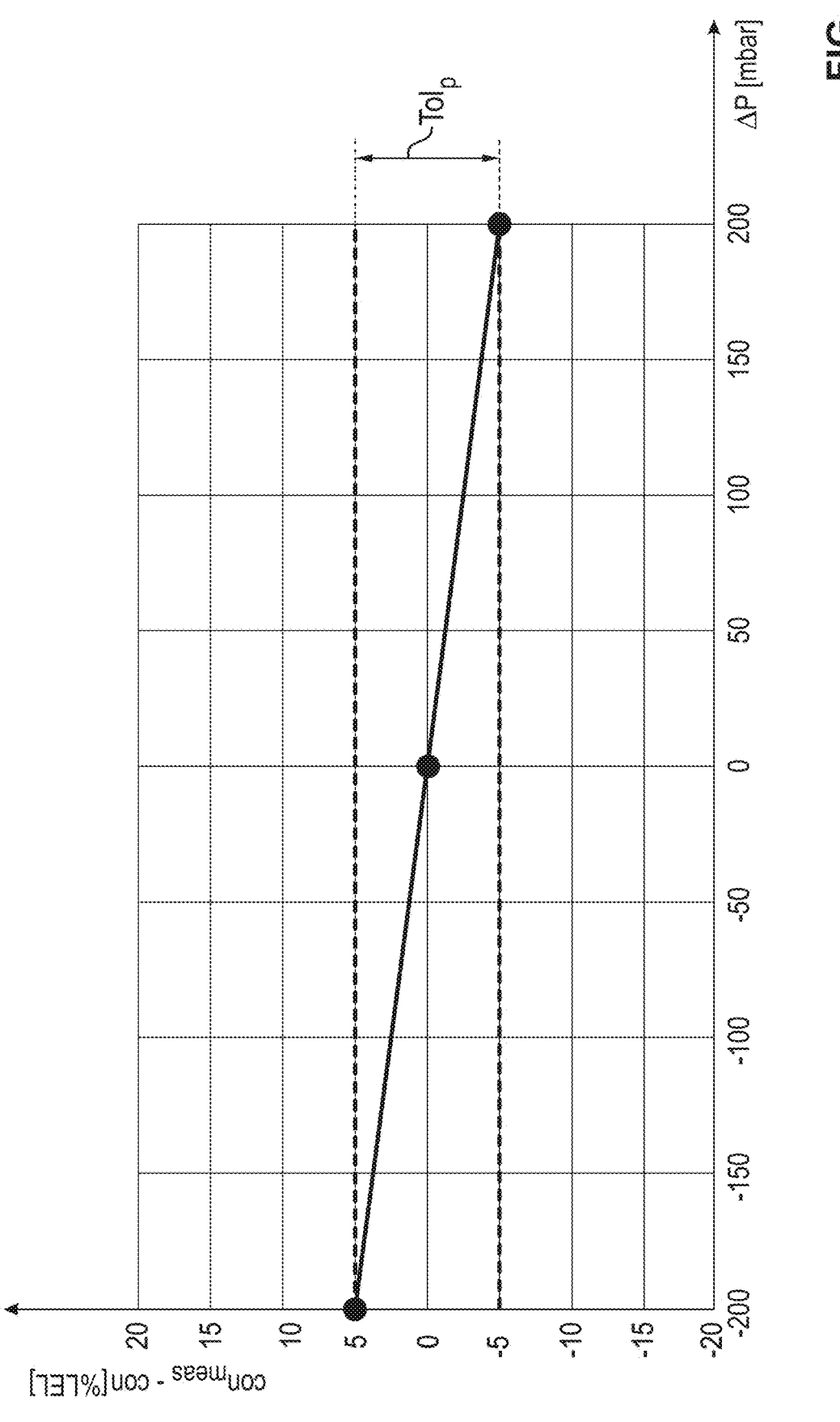
FIG. 6 is a graph showing a boundary condition for the dependence on the ambient pressure.
Figure 7:
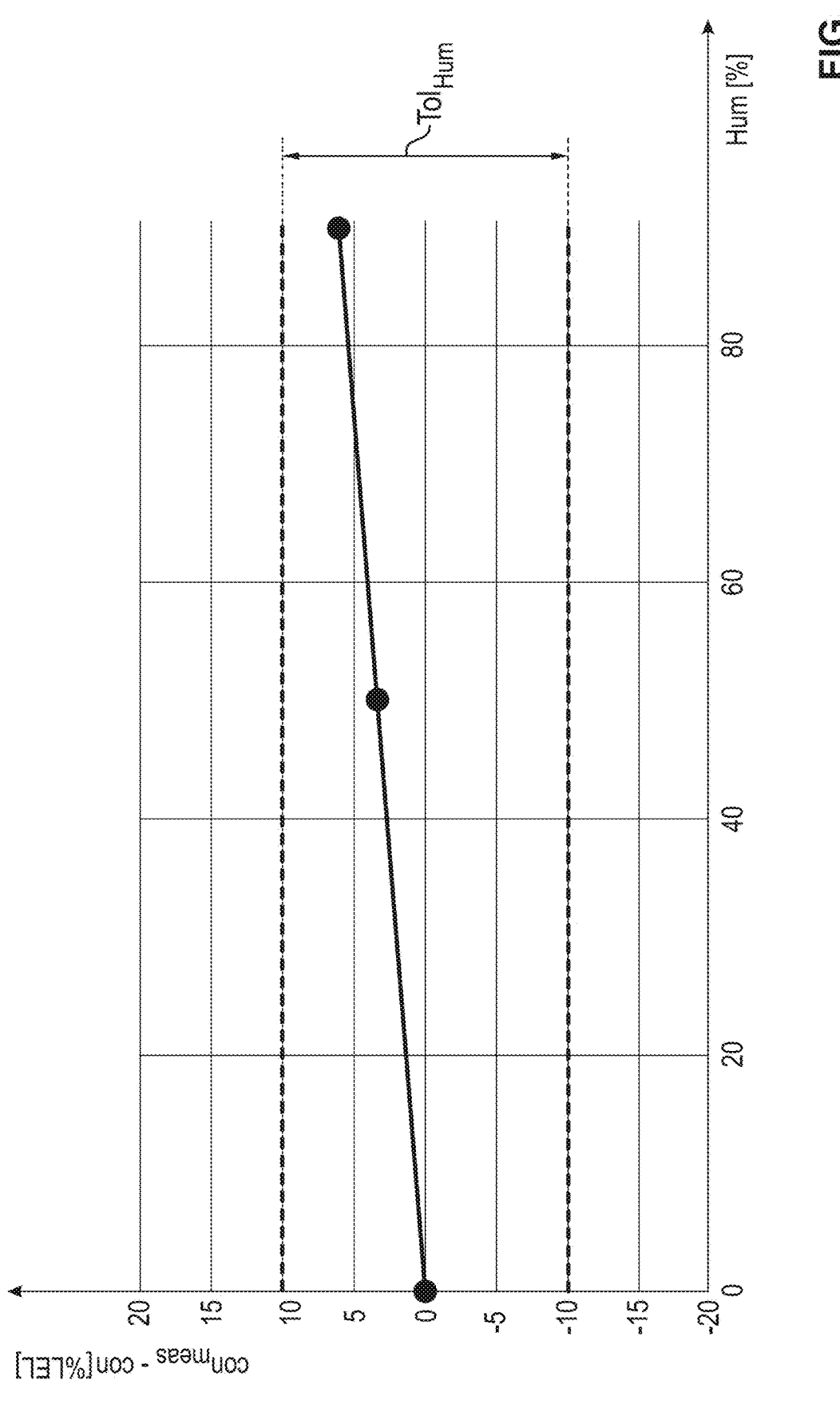
FIG. 7 is a graph showing a boundary condition for the dependence on the ambient humidity.

FIG. 5 to FIG. 7 illustrate predefined boundary conditions for how the measured value $Con_{meas}$ for the target gas concentration Con depends on the temperature difference ΔTemp (FIG. 5), the ambient pressure P (FIG. 6) and the ambient humidity Hum (FIG. 7). In this example, the calculation rule (3) with the gain factors of α=1.8 and β=−1.11 and the calculation rule (5) were applied. The deviation ΔTemp of the ambient temperature Temp from a reference ambient temperature in [degrees C.](FIG. 5), the deviation ΔP of the ambient pressure P from a specified reference pressure in [mbar](FIG. 6) and the ambient humidity Hum in [% rel. humidity] (FIG. 7) are plotted on the x-axis. The deviation between the measured value $con_{meas}$ and the actual target gas concentration con in [% LEL] is plotted on the y-axis. A tolerance band $Tol_{Temp}$ is shown for the dependence on the ambient temperature Temp, a tolerance band $Tol_P$ for the dependence on the ambient pressure P and a tolerance band $Tol_{Hum}$ for the dependence on the ambient humidity Hum.

The following is an example of how the calculation rules mentioned above are determined empirically. At least one sample is generated. In order to generate the or a sample, the gas measuring device is successively exposed to different defined test environments. Each test environment has three values temp, hum, p for the three ambient conditions temperature, humidity, pressure and a value for the target gas concentration. Each generated sample element comprises a resulting signal value u(Δtemp) of the temperature sensor 14, if the corresponding sensors are present, a resulting signal value u(hum), u(Δp) of the humidity sensor 17 and the pressure sensor 18, and a value con for the target gas concentration Con.

Each definition of a calculation rule (1) to (5) leads to the following for each sample element a resulting signal value u10 of the detector detection variable U10 and u11 of the compensator detection variable U11 and a resulting signal value u(det) of the total detection variable Det.

Various configurations described below reduce the effort required to determine the calculation rules used.

Preferably, the same function $F_{Con}$ is determined for each mode in the calculation rule (4), for which the sample is used. Using the sample, the functions $F_P$, $F_{P\_Hum}$, $F_{Hum}$ or $F_{Hum\_P}$ are also determined in the calculation rule (1).

Preferably, the values for the ambient temperature Temp in the sample cover the entire range of values from $Temp_{min}$ to $Temp_{max}$. At least when the gas measuring device 100 is to be used in the pressure-compensating or the pressure-optimized mode, the values for the ambient pressure P in the sample cover the entire range of values from $P_{min}$ to $P_{max}$. Accordingly, at least when the gas measuring device 100 is to be used in the humidity-compensating or the humidity-optimized mode, the values for the ambient humidity Hum in the sample cover the entire range of values from $Hum_{min}$ to $Hum_{max}$. Preferably, the values for the actual target gas concentration in the sample cover the entire range of values at which the gas measuring device 100 can be used.

In many cases, the functions $F_P$, $F_{P\_Hum}$, $F_{Hum}$ or $F_{Hum\_P}$ in the calculation rule (1) and the function $F_{Con}$ in the calculation rule (4) depend monotonically on the arguments. In particular this feature applies to the functions (2), (3) and (5), which each depend linearly on their arguments. Therefore, in many cases it is sufficient to use in the sample for each ambient condition Temp, Hum, P and for the target gas concentration Con the two extremal values and at least one, preferably at least three intermediate values. If, for example, one intermediate value is used, the sample has 3^4=81 sample elements.

In one embodiment, a sub-sample with several sample elements is selected from the sample. This sub-sample comprises different values for the target gas concentration. The sub-sample is used to empirically determine the function in the calculation rule (4), for example the factor $\gamma_{Con}$ in the calculation rule (5). The remaining sample elements are used to determine the functions $F_P$, $F_{P\_Hum}$, $F_{Hum}$ and/or $F_{Hum\_P}$. The calculation rule (4), which was determined using the partial sample, is retained. Each remaining sample element therefore provides a calculated value $con_{meas}$ for the target gas concentration Con.

The following is an example of how values for the parameters of calculation rule (2) are derived. In this derivation, it is assumed that the three ambient conditions Temp, P, Hum and the actual target gas concentration Con act independently of each other on the total detection variable Det and thus on the measured target gas concentration $Con_{meas}$. It is also assumed that the ambient temperature Temp has an approximately linear effect on the total detection variable Det and thus on the measured target gas concentration $Con_{meas}$, so that the influence of the ambient temperature Temp can be compensated for sufficiently accurately with the factor 3. In many cases, these assumptions correspond sufficiently accurately to reality.

First, a so-called zero point adjustment (calibration) is carried out. This zero-point adjustment is explained using the example of calculation rule (2). Here, the gas measuring device 100 is exposed to a defined reference test environment $Cond_{Ref}$. The reference test environment $Cond_{Ref}$ has a reference concentration $con_{Ref}$ of target gas to be detected, a reference ambient temperature $temp_{Ref}$, a reference ambient pressure $p_{Ref}$, and a reference ambient humidity $hum_{Ref}$. For example, $con_{Ref}=0$ and $hum_{Ref}=0\%$, so the target gas concentration Con and the ambient humidity Hum assume the respective lowest possible value.

In one implementation, the factor $\beta_{Ref}$ is initially set to 0, i.e. the influence of the ambient temperature Temp and therefore the signal U($\Delta$Temp) are initially neglected. The factor $\alpha_{Ref}$ is initially set to 1, i.e. the total detection variable Det depends on the difference between the two voltages U10 and U11. During the zero point adjustment, the factors $\alpha_{Ref}$ and $\beta_{Ref}$ can take on other values. The zero value x0 is always set so that the total detection variable Det and thus the measured target gas concentration $Con_{meas}$ for the reference test environment $Cond_{Ref}$, i.e. in the absence of combustible target gas, assume the value 0.

A value for the factor $\gamma_{con}$ is then determined empirically in the calculation rule (5). The reference test environment $Cond_{Ref}$ is modified in such a way that it has different target gas concentrations con(1), . . . one after the other. For each target gas concentration con(1), . . . , the gas measuring device 100 provides a value det(1), . . . for the total detection variable Det. For this purpose, the gas measuring device 100 uses the factors $\alpha_{Ref}$, $\beta_{Ref}$ and x0 that have just been determined or set. This procedure provides a random sample $\{[con(1), det(1)], \ldots\}$. The factor $\gamma_{con}$ is determined using this sample with the help of a regression analysis.

Figure 8:
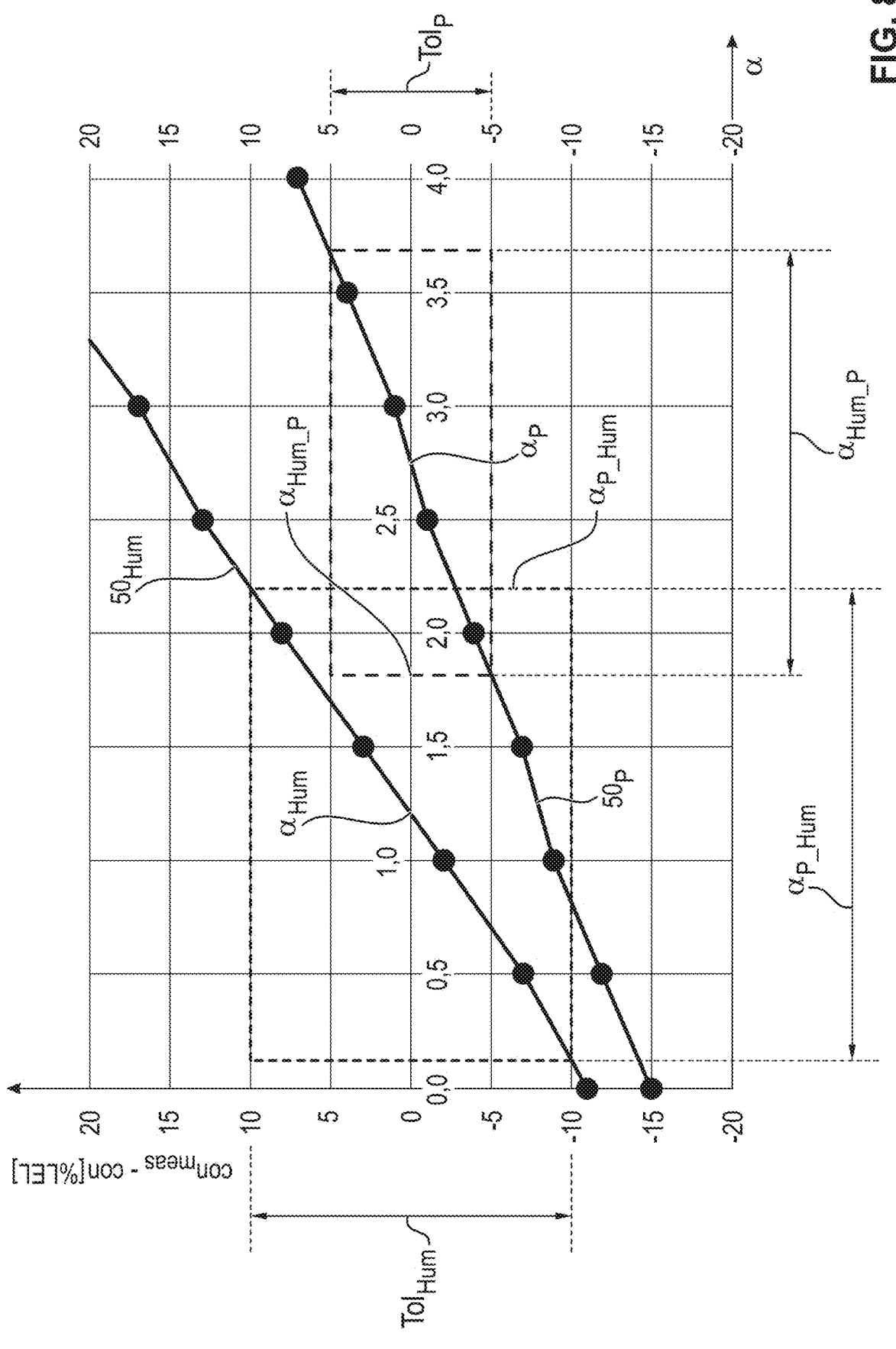
FIG. 8 is a graph showing two measurement curves as a function of a gain (amplification) factor for the compensator.
Figure 9:
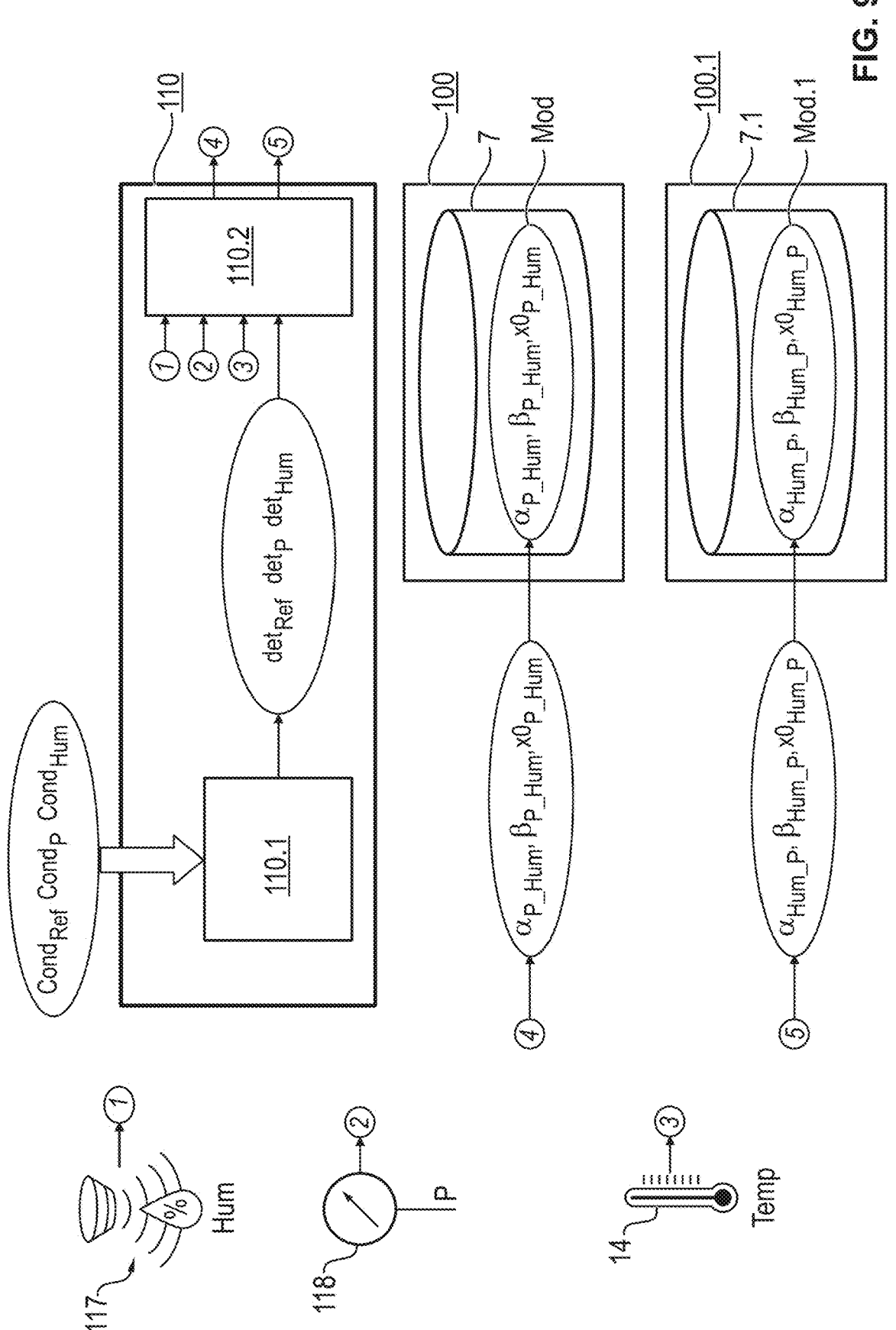
FIG. 9 is a schematic view showing a calibration device that adapts two gas measuring devices to two different modes.

Now, at least one test environment that has been modified compared to the reference test environment $Cond_{Ref}$ is created by changing at least one ambient condition. FIG. 8 and FIG. 9 illustrate an exemplary procedure in which the gas measuring device 100 is exposed to two different defined test environments $Cond_{Hum}$ and $Cond_P$. FIG. 9 shows a calibration device 110 with a first component 110.1 and a second component 110.2 as well as a further gas measuring device 100.1, wherein the gas measuring device 100.1 is identical in construction to the gas measuring device 100.

The test environment $Cond_{Hum}$ has a significantly higher ambient humidity Hum than the reference test environment $Cond_{Ref}$, while the other ambient conditions Con, Temp, P are the same. For example, the relative ambient humidity Hum in the reference test environment $Cond_{Ref}$ is 0% and in the test environment $Cond_{Hum}$ 90%, which is the highest value at which the gas measuring device 100 can still be used. The test environment $Cond_P$ has a significantly higher or even lower ambient pressure P than the reference test environment $Cond_{Ref}$, while the other ambient conditions Con, Temp, Hum are the same. For example, the test environment $Cond_P$ has an ambient pressure P that is 200 mbar higher than the reference test environment $Cond_{Ref}$.

The gas measuring device 100 provides a value u10 ($Cond_{Hum}$), u11 ($Cond_{Hum}$), u($\Delta$Temp) ($Cond_{Hum}$) for the three signals U10, U11, U($\Delta$Temp) in the test environment $Cond_{Hum}$, and a value u10($Cond_P$), u11($Cond_P$), u($\Delta$Temp) ($Cond_P$) in the test environment $Cond_P$. First, the values $\beta_{Ref}$ and $\gamma_{Con}$, which have been determined or set as described above, are used. A value is determined for the gain factor $\alpha$, which is described below. The zero value x0 is set so that a target gas concentration of zero is measured in the reference test environment $Cond_{Ref}$, i.e. in the absence of combustible target gas.

FIG. 8 shows two measurement curves 50$_P$, 50$_{Hum}$, which were generated with the same gas measuring device 100. The gain factor $\alpha$ is plotted on the x-axis and the resulting deviation of the measurement result $con_{meas}$ from the actual target gas concentration con in % LEL (Lower Explosive Limit) is plotted on the y-axis, whereby this deviation $con_{meas}$–con depends on the gain factor $\alpha$. The calculation rules (3) and (5) were applied for this purpose. Therefore, a positive or negative deviation of the measured target gas concentration $Con_{meas}$ from the actual target gas concentration Con can occur. The measurement curve 50$_P$ was obtained in the test environment $Cond_P$, the measurement curve 50$_{Hum}$ in the test environment $Cond_{Hum}$.

It can be seen that the measurement curve 50$_{Hum}$ intersects the x-axis at $\alpha_{Hum}=1.2$. This means: At the value $\alpha_{Hum}=1.2$ for the gain factor $\alpha$ and at the resulting zero value $x0_{Hum}$, the gas measuring device 100 provides the correct value 0 for the target gas concentration Con. This applies to the test environment $Cond_{Hum}$. In many cases, the assumption is justified that the value $\alpha_{Hum}=1.2$ leads to a correct value for the target gas concentration Con even at a lower ambient humidity Hum. The value $\beta$, which compensates for the influence of the ambient temperature Temp, is then set, for example by exposing the gas measuring device 100 to a different ambient temperature and checking the resulting measured value $con_{meas}$. This procedure provides a set $\alpha_{Hum}$, $\beta_{Hum}$, $x0_{Hum}$ of parameter values. This set of parameter values is used for the humidity-optimized mode Hum In FIG. 8, the measurement curve 50$_P$ shows that the humidity-optimized Hum mode leads to an incorrect measured value at a changed pressure P, namely $con_{meas}$–con=–8.5 LEL. This is accepted in some applications, for example when the gas measuring device 100 is used in a test chamber with strongly varying ambient humidity Hum. In humidity-compensating mode Hum_P, on the other hand, a specified boundary condition regarding the ambient pressure P should be maintained. The measured target gas concentration $Con_{meas}$ should differ from the actual target gas concentration Con by a maximum of 5% LEL at any ambient pressure P and therefore also at any pressure difference $\Delta$P. This boundary condition is illustrated in FIG. 8 by a tolerance band $Tol_P=+-5\%$ LEL around the x-axis. The influence of the ambient humidity Hum should be compensated as best as possible in the humidity-compensating mode Hum_P while complying with this boundary condition. As can be seen from FIG. 8, adherence with this boundary condition leads to a value $\alpha_{Hum\_P}=1.8$ LEL. A set of parameter values $\alpha_{Hum\_P}$, $\beta_{Hum\_P}$, $x0_{Hum\_P}$ for the Hum_P humidity-compensating mode is derived.

The measurement curve 50$_P$ intersects the x-axis at $\alpha_P=2.8$. This value is used for the pressure-optimized mode P. A set of parameter values $\alpha_P$, $\beta_P$, $x0_P$ for the pressure-optimized mode P is derived. For the pressure-compensating mode P_Hum, the boundary condition is used that the measured target gas concentration $Con_{meas}$ should deviate from the actual target gas concentration Con by a maximum of 10% LEL for each ambient humidity Hum. This boundary condition is indicated in FIG. 8 by the tolerance band $Tol_{Hum}$. This boundary condition leads to a value $\alpha_{P\_Hum}=2.3$ for the pressure-compensating mode P_Hum. A set of parameter values $\alpha_{P\_Hum}$, $\beta_{P\_Hum}$, $x0_{P\_Hum}$ for the pressure-compensating mode P_Hum is derived.

As already explained, in many cases the assumption is justified that the target gas concentration Con acts on the detection variables U10, U11, U($\Delta$Temp) independently of the ambient conditions Temp, P, Hum. Therefore, the calculation rule (5) with the already determined factor $\gamma_{Con}$ is preferably used. It is also possible to empirically determine a factor $\gamma_{Con}$ for each mode.

FIG. 9 shows an example of how two gas measuring devices 100 and 100.1 are calibrated using a calibration device 110 before they are used for the first time. The two gas measuring devices 100 and 100.1 are identical in construction and in particular have the same detectors and compensators. For example, they are constructed as described with reference to FIG. 1, but do not necessarily include a switch 16. The gas measuring device 100 is to be operated in the pressure-compensating mode P_Hum, the gas measuring device 100.1 in the humidity-compensating mode Hum_P. The calibration device 110 provides a set $\alpha_{P\_Hum}$, $\beta_{P\_Hum}$, $x0_{P\_Hum}$ of parameter values for the pressure-compensating mode P_Hum and a set $\alpha_{Hum\_P}$, $\beta_{Hum\_P}$, $x0_{Hum\_P}$ of parameter values for the humidity-compensating mode Hum_P. To derive these two sets of parameter values, the gas measurement device 100 is used with the temperature sensor 14. In addition, a humidity sensor 117 and a pressure sensor 118 are used to create the respective test environment $Cond_{Ref}$, $Cond_P$, $Cond_{Hum}$. The two sensors 117 and 118 are robust and reliable and are only used for calibration and are not components of the gas measuring devices 100, 100.1.

In the procedure just described, the calculation rules (3) and (5) are used, and three different test environments $Cond_{Ref}$, $Cond_P$, $Cond_{Hum}$ are used. In many cases, this procedure leads to a gas measuring device 100, 100.1 which is configured to measure the target gas concentration Con with sufficient accuracy in the respective mode. A procedure that is more generally applicable is described below. This procedure requires more effort and computing time.

First, the calibration for mode P is described, i.e. in the mode in which the influence of the ambient pressure P is compensated as best as possible. In the position shown in FIG. 1, the switch 16 is set to this mode P.

The following is an example of how the function $F=F_P$ is determined empirically. A first sample of measured values is determined. The following conditions are preferably established for the first sample of measured values: No combustible target gas is present, i.e. the target gas concentration is zero. The ambient humidity Hum assumes a constant value $hum_0$, for example 0%. The ambient pressure P assumes M different values p(1), . . . , p(M) from the value range from $P_{min}$ to $P_{max}$, the ambient temperature N assumes different values temp(1), . . . , temp(N) from the value range from $Temp_{min}$ to $Temp_{max}$. Preferably, N<M. It is possible that N equals 1, i.e. that the ambient temperature Temp is the same for all values of the first sample of measured values. The M values p(1), . . . , p(M) for the ambient pressure P and the N values temp(1), . . . , temp(N) for the ambient temperature Temp are selected so that these values can actually occur during use.

A total of M*N different conditions are therefore produced for the first sample of measured values. Each condition $x_{i,j}$ (i=1, . . . , M; j=1, . . . , N) specifies a constant target gas concentration con(1) [preferably con(1) equal to zero], an ambient pressure p(i), an ambient temperature temp(j) and the ambient humidity hum(1). The gas measuring device 100 is successively exposed to these M*N different conditions $x_{1,1}$, . . . , $x_{M,N}$ and the three detection variables U10, U11, U($\Delta$Temp) are measured. Each condition $x_{i,j}$ leads to three measured values $u10(x_{i,j})$, $u11(x_{i,j})$, $u(\Delta Temp)(x_{i,j})$ for the three variables U10, U11, U($\Delta$Temp). The first sample of measured values therefore consists of M*N sample elements, whereby each sample element has the form $$\{[u10(x_{i,j}), u11(x_{i,j}), u(\Delta Temp)(x_{i,j})];[p(i), \Delta temp(j), hum(1)]\}. \tag{6}$$

As already explained above, the function $F=F_P$ in the calculation rule (1) depends on several parameters Par(1), . . . , Par(x), x>=2. If, for example, the calculation rule (3) is used, these are the x=3 parameters $\alpha=\alpha_P$, $\beta=\beta_P$, $x0=x0_P$ or, if the zero value x0 is constant, the two parameters $\alpha=\alpha_P$ and $\beta=\beta_P$. If each parameter par(1), . . . , par(x) in the function $F_P$ is assigned a value par(1), . . . , par(x) and then the calculation rule (1) is applied to a triple [$u10(x_{i,j})$, $u11(x_{i,j})$, u($\Delta$Temp)($x_{i,j}$)], the application returns a value $$det(x_{i,j}) = F_P[u10(x_{i,j}), u11(x_{i,j}), u(\Delta Temp)(x_{i,j})] \tag{7}$$

for the total detection variable Det. This provides an initial detection variable sample with M*N sample elements, where each sample element has the form $$\{det(x_{i,j});[u10(x_{i,j}), u11(x_{i,j}), u(\Delta Temp)(x_{i,j})]\} \tag{8}$$

with (i=1, . . . , M; j=1, . . . , N).

When operating in mode P, the influence of the ambient pressure P should be compensated for as far as possible by calculation. This means: The total detection variable Det is determined in such a way that it depends as little as possible, ideally not at all, on the ambient pressure P. It is accepted that it depends relatively strongly on the ambient humidity Hum and at least somewhat on the ambient temperature Temp.

In order to determine the total detection variable Det for operation in mode P, x values par(1), . . . , par(x) are to be determined for the x parameters par(1), . . . , par(x) of the function $F_P$. Each set par(1), . . . , par(x) of parameter values leads to an empirical variance Var=Var[par(1), . . . , par(x)] of the resulting first detection variable sample. The parameter values par(1), . . . , par(x) are determined in such a way that they lead to a minimum empirical variance Var in the first detection variable sample. To determine the parameter values par(1), . . . , par(x), a target function is therefore numerically minimized. The variables of these target functions are the x parameters Par(1), . . . , Par(x) of the function $F_P$. The target function is an indicator of the empirical variance Var of the total detection variable Det=$F_P$ [U10, U11, U($\Delta$Temp)].

This procedure is explained by way of example for the preferred embodiment that the calculation rule (3) is used. Each value triplet for the three parameters $\alpha_P$, $\beta_P$, $x0_P$ leads to a value var for the empirical variance Var of the resulting first detection variable sample. The following applies $$\det(x_{i,j}) = u10\,(x_{i,j}) - \alpha_P * u11\,(x_{i,j}) - \beta_P * u\,(\Delta Temp\,(x_{i,j})) - x0_P \qquad (9)$$

The target function to be minimized is therefore the indicator of the empirical variance Var of the total detection variable Det=U10–$\alpha_P$*U11–$\beta_P$*U($\Delta$Temp)–x0$_P$. as a function of the three parameters $\alpha_P$, $\beta_P$, $x0_P$.

The difference between the largest value max $\{\det(x_{i,j})$, where i=1, . . . , M; j=1, . . . , N$\}$ and the smallest value min $\{\det(x_{i,j})$, where i=1, . . . , M; j=1, . . . , N$\}$ for the total detection variable Det can be used as an indicator of the empirical variance Var. It is also possible to use the following calculation rule:

$$Var = \frac{1}{M*N - 1} \sum_{i=1}^{M} \sum_{j=1}^{N} [\det(x_{i,j}) - \det_{avg}]^2 \qquad (10)$$

with $$\det_{avg} = \frac{1}{M*N} \sum_{i=1}^{M} \sum_{j=1}^{N} \det(x_{i,j}) \qquad (11)$$

The two-stage procedure described below significantly reduces the calculation effort. In many cases, it leads to a similarly good result for mode P.

The function $F_P$ of the calculation rule (1) is simplified and divided into two functions, namely $$Det = F_{P,10,11}\,[U10,\ U11] - F_{P,Temp}\,[U(\Delta Temp)]. \qquad (12)$$

The two functions $F_{P,10,11}$ and $F_{P,Temp}$ each depend on at least one parameter. A special form of (12) is the calculation rule (3) with $$F_{P,10,11}\,[U10,\ U11] = U10 - \alpha_P * U11 - x0_P \text{ and} \qquad (13)$$

$$F_{P,Temp}\,[U(\Delta Temp)] = \beta_P * U(\Delta Temp). \qquad (14)$$

First, a value is defined for the or each parameter of the function $F_{P,10,11}$. In the configuration according to the calculation rule (3), a value is defined for each of the parameters $\alpha_P$ and $x0_P$. For this purpose, a reduced first detection variable sample is used, in which the measured values of the temperature sensor 14 are omitted. Each sample element of this reduced detection variable sample therefore has the form $$\{\det(x_{i,j});\ [u10\,(x_{i,j}),\ u11\,(x_{i,j})]\}. \qquad (14)$$

With the help of this reduced first detection variable sample, the respective value for the or each parameter of the function $F_{P,10,11}$ is determined in such a way that the indicator for the empirical variance Var is minimized.

The function $F_{P,10,11}$ is now defined. This function $F_{P,10,11}$ is applied to the reduced detection variable sample. To be more precise: The function $F_{P,10,11}$ is applied to the respective two values $u10(x_{i,j})$, $u11(x_{i,j})$ in each sample element of the form (8), namely $$\{[\det(x_{i,j});\ [u10\,(x_{i,j}),\ u11\,(x_{i,j}),\ u(\Delta Temp)\,(x_{i,j})]\} \qquad (8)$$

is used. With the designation $\det_{P,10,11}\,(x_{i,j})=F_{P,10,11}\,[u10\,(x_{i,j}),\ u11(x_{i,j})]$, a reduced second detection variable sample is generated in which each sample element has the form $$\{[\det(x_{i,j});\ [\det_{P,10,11}\,(x_{i,j}),\ u(\Delta Temp)\,(x_{i,j})]\}. \qquad (15)$$

This sample is used to determine a value for the or each parameter of the function $F_{P,Temp}$. In the case of calculation rule (3), this is a value for the single parameter $\beta_P$. The or each value is again set so that the indicator of variance Var is minimized.

In a further simplification, the zero value $x0_P$ is determined under typical ambient conditions and depending on a gain factor $\alpha$. The ambient conditions are, for example, 20° C., 1000 mbar and 0% relative humidity. The two detection variable samples just described are used to first calculate the gain factor $\alpha_P$ for the compensator voltage U11 and then the gain factor $\beta_P$ for the measured ambient temperature U($\Delta$Temp). The previously used zero value x0 is used here without changing it.

Different variants of this procedure are possible.

As described above, a first detection variable sample is derived from the first measured value sample, wherein the first measured value sample has the form (6) and the first detection variable sample has the form (7) and each sample has M*N sample elements. It is also possible to derive a first concentration sample with M*N sample elements from the first measured value sample, with each sample element having the form $$con\,(x_{i,j}) = F_{Con}\,\{F_P\,[u10\,(x_{i,j}),\ u11\,(x_{i,j}),\ u(\Delta Temp)\,(x_{i,j})]\} \qquad (16)$$

with (i=1, . . . , M; j=1, . . . , N).

In one embodiment, a second sample of measured values is determined in addition to the first. Just as with the first sample of measured values, the ambient humidity Hum assumes the constant value hum$_0$, the ambient pressure P M assumes different values and the ambient temperature Temp N assumes different values. In contrast to the first sample of measured values, however, combustible target gas is present in the environment. The function, which is derived empirically with the help of the first sample of measured values, is designated $F_{P,0}$. A function $F_{P,con}$ is derived empirically using the second sample of measured values. The applied function F is derived by a suitable averaging of the two functions $F_{P,0}$ and $F_{P,con}$.

The configuration for the P_Hum mode is now described. The measured value con$_{meas}$ for the target gas concentration Con$_{meas}$ should vary by a maximum of x % depending on the ambient humidity Hum if the ambient humidity Hum remains within a specified humidity range.

Again, the first sample of measured values is used, i.e. a sample with sample elements, where each sample element has the form (6), i.e.

$$\{[u10\,(x_i),\,u11\,(x_i),\,u(\Delta Temp)\,(x_i)];\,[\Delta temp\,(i),\,p\,(i),\,hum\,(1)]\}.\qquad(6)$$

The first sample of measured values has the same ambient humidity $hum(x_1)$ throughout.

In addition, K-1 further samples of measured values are generated, K>=2. For each second sample, a value $hum(2),\,\ldots,\,hum(K)$ is set for the ambient humidity Hum throughout, whereby the total of K values $hum(1),\,\ldots,\,hum(K)$ are all different from each other. The first sample was generated at M*N conditions $x_{i,j,1}=x_{i,j}$ (i=1, ..., M*N), where the ambient conditions were con(1), p(i), $\Delta temp(j)$, hum(1) (i=1, ..., M; j=1, ..., N). For each additional sample, the M*N conditions $x_{i,j,k}$ (i=1, ..., M; j=1, ..., N; k=2, ..., K) are present.

In total, there are K samples, each with M*N sample elements, whereby sample no. k has the form $$[u10\,(x_{i,j,k}),\,u11\,(x_{i,j,k}),\,u(\Delta Temp)\,(x_{i,j,k})];\qquad(17)$$

$$[p(i),\,\Delta temp(j),\,hum(k)]\}\,\big(i = 1,\,\ldots,\,M;\,j = 1,\,\ldots,\,N;\,k = 1,\,\ldots,\,K\big).$$

In P_Hum mode, the evaluation unit 9 applies the calculation rule $$Det = F_{P\_Hum}\,[U10,\,U11,\,U\,(\Delta Temp)].\qquad(18)$$

Preferably, the calculation rule (18) has the form $$Det = U10 - \alpha_{P\_Hum} * U11 - \beta_{P\_Hum} * U\,(\Delta Temp) - x0_{P\_Hum}.\qquad(19)$$

Values are to be calculated for the x parameters Par(1), ..., Par(x) of the function $F_{P\_Hum}$.

The derivation of a first detection variable sample was described above with reference to the calculation rule (7). This procedure is modified. Accordingly, K detection variable samples are derived. Each detection variable sample has M*N sample elements, where each sample element has the form $$det\,(x_{i,j,k}) = F_{P\_Hum}\,[u10\,(x_{i,j,k}),\,u11\,(x_{i,j,k}),\,u\,(\Delta Temp)\,(x_{i,j,k})].\qquad(20)$$

The above-mentioned boundary condition that the measured value con for the target gas concentration Con should vary by a maximum of x % depending on the ambient humidity Hum leads to a boundary condition for the total detection variable Det, which should vary by a maximum of y % depending on the ambient humidity Hum. The factor y depends on the specified functional relationship between the target gas concentration Con and the total detection variable Det, whereby this relationship is described by the calculation rule (4), in particular by the calculation rule (5). For example, the total detection variable Det should lie within a tolerance band of width y % when the ambient humidity Hum fluctuates. This leads, for example, to the requirement $$(1 - y) * det_{avg} < \, = det\,(x_{i,j,k}) <= (1 + y) * det_{avg}\qquad(21)$$

for all i=1, ..., M; j=1, ..., N; k=1, ..., K, wherein $det_{avg}$ is the mean value of all sample elements of the detection variable sample(s).

The parameter values par(1), ..., par(x) for the function $F_{P\_Hu}m$ of the calculation rule (18) are defined in such a way that the boundary condition (21) is met.

While specific embodiments of the invention have been shown and described in detail to illustrate the application of the principles of the invention, it will be understood that the invention may be embodied otherwise without departing from such principles.

| List of reference symbols | |
|---|---|
| 100 | Gas measuring device, comprises the detector 10, the compensator 11, the temperature sensor 14, the control unit 6 and the data memory 7 as well as optionally the humidity sensor 17 and the pressure sensor 18 |
| 2 | Optional flame protection in front of openings Ö1, Ö2 |
| 5 | Compensator chamber, surrounds the compensator 11 |
| 6 | Control unit, receives signals from sensors 12.1, 12.2, 13.1, 13.2, 14 |
| 7 | Data memory in which the model Mod is stored |
| 7.1 | Data memory of the additional gas measuring device 100.1, in which the model Mod.1 is stored |
| 8 | Detector chamber, surrounds the detector 10 |
| 9 | Evaluation unit, belongs to control unit 6, derives the target gas concentration $Con_{meas}$ |
| 10 | Detector, comprises the heating segment 20 |
| 11 | Compensator, comprises the heating segment 38 |
| 12.1 | Voltage sensor, measures the voltage U10 |
| 12.2 | Voltage sensor, measures the voltage U11 |
| 13.1 | Amperage sensor, measures the current I.1 |
| 13.2 | Amperage sensor, measures the current I.2 |
| 14 | Temperature sensor, measures the difference $\Delta Temp$ between the ambient temperature and a reference temperature |
| 16 | Selection unit in the form of a switch with which a user can select a mode |
| 17 | Humidity sensor of the gas measuring device 100, measures the ambient humidity Hum |

-continued

| List of reference symbols | |
| --- | --- |
| 18 | Pressure sensor of the gas measuring device 100, measures the pressure difference ΔP |
| 20 | Heating segment of the detector 10 |
| 24 | Electrical contacts for the heating detector segment 20 |
| 25 | Ceramic coating (sheathing) around the heating detector segment 20 |
| 26 | Catalytic coating on the ceramic coating 25 |
| 27 | Mounting plate of the detector 10 |
| 30 | Electrically conductive component in the form of a conductor track of the detector 10 configured as a flat component |
| 31 | Support plate for component 30 |
| 32 | Heating segment, belongs to component 30 |
| 33 | Wafer substrate, supports the carrier plate 31 |
| 34 | Electrical contact points 34 for the component 30 |
| 35 | Protective coating on the component 30 |
| 38 | Heating segment of the compensator 11 |
| 43, 44 | Voltage sources |
| 46 | Electrical contacts for component 30 |
| $50_{Hum}$ | Dependence of the measurement error $Con_{meas}$ – Con on the gain factor α in the test environment $Cond_{Hum}$ |
| $50_P$ | Dependence of the measurement error $Con_{meas}$ – Con on the gain factor α in the test environment $Cond_P$ |
| 100 | Gas measuring device |
| 100.1 | Further gas measuring device |
| 110 | Calibration device, generates the models Mod and Mod.1, comprises the humidity sensor 117 and the pressure sensor 118, comprises the components 110.1 and 110.2 |
| 117 | Humidity sensor of the calibration device 110 |
| 118 | Pressure sensor of the calibration device 110 |
| α | Gain factor for the compensator voltage U11 in the total detection variable Det |
| $α_{Hum}$ | Gain factor for humidity-optimized mode |
| $α_{Hum\_P}$ | Gain factor for the humidity-compensating mode |
| $α_P$ | Gain factor for print-optimized mode |
| $α_{P\_Hum}$ | Gain factor for the pressure-compensating mode |
| β | Gain factor for the signal U(ΔTemp) in the total detection variable Det |
| B | Spatial area to be monitored for the presence of a combustible target gas |
| Con | Actual target gas concentration |
| $Con_{meas}$ | Target gas concentration derived from the gas measuring device 100 |
| $Cond_{Hum}$ | Test environment with an ambient humidity Hum of 90% relative humidity |
| $Cond_P$ | Test environment with an ambient pressure increased by 200 mbar P |
| $Cond_{Ref}$ | Reference test environment with an ambient humidity hum of 0% relative humidity and a target gas concentration con of 0% LEL |
| Det | Total detection variable, depends on U10, U11 and U(ΔTemp), optionally also on U(Hum) and U(ΔP) |
| Gp | Gas sample from area B |
| Hum | Ambient humidity, and also humidity-optimized mode at the same time |
| Hum_P | Humidity-compensating mode |
| I.1 | Amperage of the current flowing through the detector 10 |
| I.2 | Amperage of the current flowing through the compensator 11 |
| Mod | Computer-evaluable model with functional relationships between the detection variables U10 and U11, the signal U(ΔTemp) and the target gas concentration $Con_{meas}$, is applied by the evaluation unit 9 |
| Mod.1 | Computer-evaluable model, which is used by the evaluation unit of the further gas measuring device 100.1, is stored in the data memory 7.1 |
| Ö1 | Opening the detector chamber 8 |
| Ö2 | Opening the compensator chamber 5 |
| P | Ambient pressure, and also pressure-optimized mode at the same time |
| P_Hum | Pressure-compensating mode |
| ΔP | Difference between the ambient pressure P and a specified reference pressure, measured by the pressure sensor 18 |
| Temp | Ambient temperature |
| ΔTemp | Difference between the current ambient temperature Temp and a specified reference temperature, measured by temperature sensor 14 |
| U10 | Electrical voltage applied to the detector 10 |
| U11 | Electrical voltage applied to the compensator 11 |

-continued

| List of reference symbols | |
|---|---|
| U($\Delta$Temp) | Signal supplied by temperature sensor 14, correlated with the temperature difference $\Delta$Temp |
| x0 | Constant in the total detection variable Det |

What is claimed is:

1. A gas measuring device, which is configured to measure a concentration of a combustible target gas in a spatial area, the gas measuring device comprising:

a detector having a detector detection variable;

a compensator having a compensator detection variable;

a detector detection variable sensor configured to measure the detector detection variable;

a compensator detection variable sensor configured to measure the compensator detection variable, wherein the gas measuring device is configured such that a gas sample from the spatial area at least temporarily reaches the detector and the compensator, wherein the measured detector detection variable is correlated with the concentration of the target gas in the gas sample, wherein the measured compensator detection variable is correlated with the concentration of the target gas in the gas sample less than the measured detector detection variable is or is not correlated with the target gas concentration, wherein the measured detector detection variable and the measured compensator detection variable are influenced or at least can be influenced by at least one ambient condition acting on the gas sample; and a signal-processing evaluation unit configured to determine the concentration of the target gas in the gas sample as a function of the measured detector detection variable and of the measured compensator detection variable, wherein the gas measuring device is configured to be operated during use in one of at least two different modes, wherein a first mode is a pressure compensating mode and a second mode is a humidity compensating mode, wherein in the pressure-compensating mode an influence of an ambient pressure on a determination result of the evaluation unit is compensated for such that a boundary condition is met that an influence of an ambient humidity on the determination result remains below a specified upper humidity influence threshold, and the influence of the ambient pressure on the determination result of the gas measuring device is compensated under this boundary condition, wherein in the humidity-compensating mode an influence of the ambient humidity on the determination result is compensated for such that a boundary condition is met that the influence of the ambient pressure on the determination result remains below a specified upper pressure influence threshold, and the influence of the ambient humidity on the determination result is compensated under this boundary condition, and wherein the evaluation unit is configured such that in the pressure-compensating mode the dependence of the determined target gas concentration on at least one of the detector detection variable and on the compensator detection variable is different from that in the humidity-compensating mode.

2. The gas measuring device according to claim 1, wherein the gas measuring device is configured to further be operated during use in at least one of a pressure-optimized mode and in a humidity-optimized mode, wherein in the pressure-optimized mode the influence of the ambient pressure on the determination result of the evaluation unit is compensated without adhering to a boundary condition, wherein in the humidity-optimized mode, the influence of the ambient humidity on the determination result is compensated without adhering to a boundary condition, and wherein the evaluation unit is configured such that in each mode the dependence of the determined target gas concentration on the detector detection variable and/or on the compensator detection variable is different than in any other mode.

3. The gas measuring device according to claim 1, wherein the gas measuring device is configured to be operated in each one of the pressure-compensating mode and the humidity-compensating mode.

4. The gas measuring device according to claim 2, wherein the gas measuring device is configured to be operated in each one of the pressure-compensating mode, humidity-compensating mode, pressure-optimized mode, and humidity-optimized mode.

5. The gas measuring device according to claim 3, further comprising a selection unit configured to capture a specification from a user or from a higher-level control system, wherein the captured specification specifies a mode in which the gas measuring device is to be operated, and wherein the gas measuring device is configured to be operated in the pressure-compensating mode or in the humidity-compensating mode depending on a captured specification.

6. The gas measuring device according to claim 4, further comprising a selection unit configured to capture a specification from a user or from a higher-level control system, wherein the captured specification specifies a mode in which the gas measuring device is to be operated, wherein the gas measuring device is configured to be operated in the pressure-compensating mode, in the humidity-compensating mode, in the pressure-optimized mode, or in the humidity-optimized mode depending on a captured specification.

7. The gas measuring device according to claim 3, wherein the gas measuring device is configured to determine an estimated value for the target gas concentration in the same gas sample in at least two different ones of the modes and to generate an alarm if at least one determined estimated value is outside a specified value range for the target gas concentration.

8. The gas measuring device according to claim 1, further comprising an ambient condition sensor configured to measure one of the ambient conditions acting on the gas sample, wherein the evaluation unit is configured to determine the concentration of the target gas in the gas sample additionally as a function of a signal of the sensor for the ambient condition.

9. The gas measuring device according to claim 8, wherein the ambient condition sensor is a temperature sensor configured to measure the ambient temperature.

10. The gas measuring device according to claim 8, wherein the ambient condition sensor is an ambient humidity sensor configured to indicate an ambient humidity or an ambient pressure sensor configured to indicate an ambient pressure, wherein the ambient condition sensor is either activated or deactivated, wherein the gas measuring device is configured such that with the ambient condition sensor being activated, the evaluation unit determines the concentration of the target gas in the gas sample additionally as a function of the signal from the activated ambient condition sensor, and wherein the gas measuring device is configured to be operated in at least one of the pressure-compensating mode and the humidity-compensating mode at least with the ambient condition sensor deactivated.

11. The gas measuring device according to claim 1, wherein the detector comprises a heatable detector, segment and the compensator comprises a heatable compensator segment, wherein the gas measuring device is configured to heat the detector segment such that the heated detector segment oxidizes combustible target gas in the gas sample and the oxidation further heats the detector segment, wherein the gas measuring device is configured to heat the compensator segment and the heated compensator segment is configured to oxidize less combustible target gas per time unit than the heated detector segment or the gas measuring device is configured to heat the compensator segment and is configured such that a smaller quantity per time unit of the gas sample reaches the compensator than the detector, wherein the detector detection variable sensor is configured to measure an indicator for a temperature of the detector segment as the detector detection variable, and wherein the compensator detection variable sensor is configured to measure an indicator for a temperature of the compensator segment as the compensator detection variable.

12. The gas measuring device according to claim 1, wherein the evaluation unit has at least temporary read access to a computer-evaluable model, wherein the model comprises a respective functional relationship for each mode in which the gas measuring device is configured to be operated, wherein the functional relationship for a mode is a relationship between the target gas concentration on the one hand and a respective signal of each detection variable sensor on the other hand, and wherein the evaluation unit is configured to determine the target gas concentration based on the functional relationship for the mode in which the gas measuring device is currently being operated in and based on a respective signal of each detection variable sensor.

13. The gas measuring device according to claim 8, wherein the evaluation unit has at least temporary read access to a computer-evaluable model, wherein the model comprises a respective functional relationship for each mode in which the gas measuring device is operable, wherein the functional relationship for a mode is a relationship between the target gas concentration, a respective signal of each detection variable sensor, and a signal from the ambient condition sensor, wherein the evaluation unit is configured to determine the target gas concentration based on the functional relationship for the mode in which the gas measuring device is currently being operated, on a respective signal of each detection variable sensor and the signal of the ambient condition sensor.

14. The gas measuring device according to claim 1 as the first gas measuring device in combination with a second gas measuring device having the features of the first gas measuring device, wherein the evaluation unit of the first gas measuring device has at least temporary read access to a first computer-evaluable model, which describes a first dependence of the target gas concentration at least on the detector detection variable and on the compensator detection variable for operation in the pressure-compensating mode, and wherein the evaluation unit of the second gas measuring device has at least temporary read access to a second computer-evaluable model, which describes a second dependence of the target gas concentration at least on the detector detection variable and on the compensator detection variable for operation in the humidity-compensating mode.

15. The gas measuring device according to claim 8, as the first gas measuring device, in combination with a second gas measuring device having the features of the first gas measuring device, wherein the evaluation unit of the first gas measuring device has at least temporary read access to a first computer-evaluable model, which describes, for operation in the pressure-compensating mode, the first dependence of the target gas concentration at least on the detector detection variable, on the compensator detection variable, and on at least one of the ambient conditions, and wherein the evaluation unit of the second gas measuring device has the at least temporary read access to a second computer-evaluable model, which describes, for operation in the humidity-compensating mode, the second dependence of the target gas concentration at least on the detector detection variable, on the compensator detection variable, and on the at least one of the ambient conditions.

16. A calibration device for calibrating the gas measuring device according to claim 12, wherein the calibration device is configured to capture a specification, wherein the captured specification specifies at least one mode in which the gas measuring device is to be operated, and wherein the calibration device is configured to generate a model that can be analyzed by a computer such that the generated model comprises a functional relationship for the selected mode, and the model is used by the evaluation unit of the gas measuring device, wherein the calibration device is configured to use a predetermined sample and a set of predetermined possible functional relationships to generate the model, wherein the sample comprises several sample elements, wherein each sample element of the sample comprises an identification of an ambient condition-target gas combination and a combination of signal values, wherein the identification identifies a combination of an ambient temperature, an ambient pressure, an ambient humidity, and an actual target gas concentration and wherein the combination of signal values has for the respective signal of each detection variable sensor a respective value measured at the ambient condition-target gas combination of the sample element, wherein for each mode, for each predetermined possible functional relationship, and for each sample element, the calibration device is configured to apply the functional relationship to the combination of signal values of the sample element and thereby calculate a value for the target gas concentration and to compare the calculated value for the target gas concentration with the actual value of the target gas combination in this sample element, and wherein the calibration device is configured to select for every mode a possible functional relationship using the comparison results and to cause the selected functional relationship to be used as the functional relationship to be applied in the mode by the evaluation unit.

17. A gas measuring process for measuring a concentration of a combustible target gas in a spatial area, the process is performed using a gas measuring device comprising a detector, a compensator, a detector detection variable sensor and a compensator detection variable sensor, wherein the detector has a detector detection variable, wherein the detector detection variable correlates with the concentration of the target gas in a gas sample, wherein the compensator has a compensator detection variable, wherein the compensator detection variable correlates less than the detector detection variable with the target gas concentration or is not correlated with the target gas concentration in the gas sample, wherein the detector detection variable and the compensator detection variable are influenced or at least can be influenced by at least one ambient condition acting on the gas sample, wherein the gas measurement process comprises the steps of:

causing a gas sample from the area to reach the detector and the compensator;

with the detector detection variable sensor, measuring the detector detection variable;

with the compensator detection variable sensor, measuring the compensator detection variable; and determining the concentration of the target gas in the gas sample as a function of the measured detector detection variable and the measured compensator detection variable, wherein, when carrying out the gas measuring process, the gas measuring device is operated in at least one of a pressure-compensating mode and a humidity-compensating mode, wherein in the pressure-compensating mode the influence of an ambient pressure on a determination result is compensated for such that a boundary condition is met that the influence of an ambient humidity on the determination result remains below a specified upper humidity influence threshold, and the influence of the ambient pressure on the determination result of the gas measuring device is compensated under this boundary condition, and wherein in the humidity-compensating mode, the influence of the ambient humidity on the determination result is compensated for such that a boundary condition is met that the influence of the ambient pressure on the determination result remains below a specified upper pressure influence threshold, and the influence of the ambient humidity on the determination result is compensated under the boundary condition, and wherein in the pressure-compensating mode the dependence of the determined target gas concentration on at least one of the detector detection variable on and the compensator detection variable is different from that in the humidity-compensating mode.

18. A calibration process for calibrating a gas measuring device, the gas measuring device being configured to measure a concentration of a combustible target gas in a spatial area, the gas measuring device comprising: a detector having a detector detection variable;

a compensator having a compensator detection variable; a detector detection variable sensor configured to measure the detector detection variable; a compensator detection variable sensor configured to measure the compensator detection variable, wherein the gas measuring device is configured such that a gas sample from the spatial area reaches the detector and the compensator, wherein the measured detector detection variable is correlated with the concentration of the target gas in the gas sample and the compensator detection variable is correlated with the concentration of the target gas in the gas sample less than the measured detector detection variable or is not correlated with the target gas concentration, wherein the measured detector detection variable and the measured compensator detection variable are influenced or at least can be influenced by at least one ambient condition acting on the gas sample; and a signal-processing evaluation unit configured to determine the concentration of the target gas in the gas sample as a function of the measured detector detection variable and of the measured compensator detection variable, wherein the gas measuring device is configured to be operated during use in one of at least two different modes, wherein a first mode is a pressure compensating mode and a second mode is a humidity compensating mode, and wherein the evaluation unit is configured to apply, for determining the concentration of the target gas, a respective functional relationship for the mode to the measured detector detection variable and to the measured compensator detection variable;

wherein the calibration process comprises the steps of:

providing a sample and a set of predefined possible functional relationships, wherein the sample comprises several sample elements, wherein each sample element of the sample includes an identification of an ambient condition-target gas combination, which comprises a combination of an ambient temperature, an ambient pressure, an ambient humidity, and an actual target gas concentration, and wherein the sample includes a combination of signal values, which comprises the respective signal value of each detection variable sensor measured at the ambient condition-target gas combination;

specifying at least one mode in which the gas measuring device is to operate be operated, and applying each specified possible functional relationship to the signal value combination of the sample element for each mode and for each sample element, thereby calculating a value for the target gas concentration;

comparing the calculated value for the target gas concentration with the actual value of the target gas combination in the sample element;

using the comparison results, selecting a possible functional relationship for each mode; and causing the selected functional relationship to be used by the evaluation unit as the functional relationship to be applied in the respective mode, wherein the selection of the functional relationship is performed such that in the pressure-compensating mode an influence of the ambient pressure on a determination result of the evaluation unit is compensated such that a boundary condition is met that an influence of the ambient humidity on the determination result remains below a specified upper humidity influence threshold, and the influence of the ambient pressure on the determination result of the gas measuring device is compensated under this boundary condition and in the humidity-compensating mode, an influence of the ambient humidity on the determination result is compensated for such that a boundary condition is met that the influence of the ambient pressure on the determination result remains below a specified upper pressure influence threshold, and the influence of the ambient humidity on the determination result is compensated under this boundary condition, and in the pressure-compensating mode the dependence of the determined target gas concentration on the detector detection variable and/or on the compensator detection variable is different from that in humidity-compensating mode.

19. The calibration process according to claim 18, wherein the gas measuring device further comprises an ambient condition sensor configured to measure an ambient condition value at the ambient condition-target gas combination, wherein the combination of signal values further comprises at least one value of the ambient condition sensor measured at the ambient condition-target gas combination.

* * * * *